(12) United States Patent
Kartalov et al.

(10) Patent No.: US 10,174,313 B2
(45) Date of Patent: *Jan. 8, 2019

(54) METHODS AND DEVICES FOR MICRO-ISOLATION, EXTRACTION, AND/OR ANALYSIS OF MICROSCALE COMPONENTS IN AN ARRAY

(71) Applicants: CALIFORNIA INSTITUTE OF TECHNOLOGY, Pasadena, CA (US); UNIVERSITY OF SOUTHERN CALIFORNIA, Los Angeles, CA (US); CURATE BIOSCIENCES LLC, San Diego, CA (US)

(72) Inventors: Emil P. Kartalov, Pasadena, CA (US); Cheng-Chung Lee, Irvine, CA (US); Paul Predki, Carlsbad, CA (US)

(73) Assignees: CALIFORNIA INSTITUTE OF TECHNOLOGY, Pasadena, CA (US); UNIVERSITY OF SOUTHERN CALIFORNIA, Los Angeles, CA (US); CURATE BIOSCIENCES LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/885,736

(22) Filed: Jan. 31, 2018

(65) Prior Publication Data

US 2018/0171331 A1    Jun. 21, 2018

Related U.S. Application Data

(63) Continuation of application No. 14/996,613, filed on Jan. 15, 2016, now Pat. No. 9,920,315.

(60) Provisional application No. 62/104,609, filed on Jan. 16, 2015.

(51) Int. Cl.
| | | |
|---|---|---|
| *C12Q 1/68* | (2018.01) | |
| *C12N 15/10* | (2006.01) | |
| *C12Q 1/686* | (2018.01) | |
| *C12Q 1/6874* | (2018.01) | |
| *B01L 3/00* | (2006.01) | |
| *C12Q 1/6853* | (2018.01) | |

(52) U.S. Cl.
CPC .... *C12N 15/1093* (2013.01); *B01L 3/502707* (2013.01); *C12Q 1/686* (2013.01); *C12Q 1/6853* (2013.01); *C12Q 1/6874* (2013.01); *B01L 2300/0816* (2013.01); *B01L 2300/0887* (2013.01)

(58) Field of Classification Search
CPC ..... B01L 2300/0816; B01L 2300/0887; B01L 3/502707; C12N 15/1093; C12Q 1/686; C12Q 1/6874
USPC ................................................ 435/6.1, 283.1
See application file for complete search history.

(56) References Cited

U.S. PATENT DOCUMENTS

| | | | |
|---|---|---|---|
| 9,920,315 B2 * | 3/2018 | Kartalov | C12N 15/1093 |
| 2005/0221281 A1 * | 10/2005 | Ho | B01L 3/5025 |
| | | | 435/4 |
| 2012/0164679 A1 * | 6/2012 | Vrouwe | B01L 3/5027 |
| | | | 435/29 |
| 2013/0005585 A1 | 1/2013 | Anderson et al. | |
| 2014/0357500 A1 | 12/2014 | Vigneault et al. | |
| 2018/0171330 A1 | 6/2018 | Kartalov et al. | |

OTHER PUBLICATIONS

Non-Final Office Action for U.S. Appl. No. 15/885,352, filed Jan. 31, 2018 on behalf of California Instiutute of Technology, dated May 24, 2018. 11 pages.
Berry, D. et al., "Barcoded Primers Used in Multiplex Amplicon Pyrosequencing Bias Amplification", Applied and Environmental Microbiology, vol. 77, No. 21, pp. 7846-7849, (2011), 5 pages.

* cited by examiner

*Primary Examiner* — Cynthia B Wilder
(74) *Attorney, Agent, or Firm* — Steinfl + Bruno, LLP

(57) ABSTRACT

Provided herein are devices and methods for the micro-isolation of biological cellular material. A micro-isolation device described can comprise a photomask that protects regions of interest against DNA-destroying illumination. The micro-isolation device can further comprise photosensitive material defining access wells following illumination and subsequent developing of the photosensitive material. The micro-isolation device can further comprise a chambered microfluidic device comprising channels providing access to wells defined in photosensitive material. The micro-isolation device can comprise a chambered microfluidic device without access wells defined in photosensitive material where valves control the flow of gases or liquids through the channels of the microfluidic device. Also included are methods for selectively isolating cellular material using the devices described herein, as are methods for biochemical analysis of individual regions of interest of cellular material using the devices described herein. Further included are methods of making masking arrays useful for the methods described herein. The micro-isolation devices can comprise a unique combination of barcodes in each microfluidics well, allowing two-dimensional mapping of genetic information.

21 Claims, 22 Drawing Sheets

METHODS AND DEVICES FOR MICRO-ISOLATION, EXTRACTION, AND/OR ANALYSIS OF MICROSCALE COMPONENTS IN AN ARRAY

CROSS REFERENCE TO RELATED APPLICATIONS

The present application is a Continuation application of Ser. No. 14/996,613 filed on Jan. 15, 2016 which, in turn, claims priority to U.S. Provisional Application 62/104,609 filed on Jan. 16, 2015, and may be related to U.S. patent application Ser. No. 14/511,778 filed on Oct. 10, 2014, and U.S. Pat. No. 8,889,416 issued on Nov. 18, 2014, all of which are incorporated herein by reference in their entirety.

STATEMENT OF GOVERNMENT GRANT

This invention was made with government support under Grant No. CA174416 awarded by the National Institutes of Health. The government has certain rights in the invention.

FIELD

The present disclosure relates to micro-isolation of microscale components such as tissue and/or cell samples. More specifically, it relates to methods and devices for such micro-isolation in an array.

BACKGROUND

The isolation of certain microscale components is an important factor in several applications where the ability to differentially analyze properties exhibited by varying types of components (e.g. cell types) is desired.

For example, the ability to recognize properties typical of a component included in a matrix with other similar components, can be of importance in various fields, including in particular biological fields. In particular, the ability to identify properties which cause a cell to behave in a certain way is expected to promote an understanding of how cells behave both normally and abnormally. For example, the ability to selectively analyze cancerous cells is expected to provide insight into the particular biochemical activities of those cells relative to normal cells.

However, separating different cell types and in particular cancerous cells from non-cancerous cells can be a difficult endeavor.

SUMMARY

Provided herein are apparatuses and methods for the micro-isolation of micro-scale components such as cellular material, which in several embodiments provide for the selective biochemical analysis of desired components.

According to a first aspect, a method is described, the method comprising: a) fabricating a distributor chip comprising: a plurality of microfluidics channels, each microfluidics channel having an input port on a first surface and a plurality of output ports on a second surface opposite the first surface, each microfluidics channel, its input port and its plurality of output ports laying on a plane parallel to a subsequent or previous microfluidics channel, thereby obtaining parallel rows of the output ports on the second surface; b) fabricating a first overlay comprising parallel rows of microfluidics wells having positions corresponding to the parallel rows of the output ports; c) fabricating a receiver chip comprising parallel rows of microfluidics conduits having positions corresponding to the parallel rows of the microfluidics wells of the first overlay; d) fabricating a stopper layer permeable to air and impermeable to water; e) providing a support layer comprising parallel rows of openings corresponding to the parallel rows of the microfluidics conduits of the receiver chip; f) positioning the distributor chip on the first overlay, the first overlay on the receiver chip, the receiver chip on the stopper layer, and the stopper layer on the support layer; g) aligning the distributor chip, the first overlay, the receiver chip, the stopper layer and the support layer, by aligning the parallel rows of the output ports, the parallel rows of the microfluidics wells, the parallel rows of the microfluidics conduits, and the parallel rows of openings, thereby creating an aligned assembly; h) inserting a solution in each input port of each microfluidics channel of the plurality of microfluidics channels, each solution comprising same reagents and a different barcode for each input port; and j) removing the first overlay from the aligned assembly, thereby obtaining parallel rows of microfluidics wells, each row having the same reagents and a unique barcode in each row of the parallel rows of microfluidics wells of the first overlay.

According to a second aspect, a method of barcoding a sample having a target sequence is described, the method comprising: providing at least one gene primer pair formed by a gene forward primer and a gene reverse primer and at least one barcode primer pair formed by a barcode forward primer and a barcode reverse primer, wherein the barcode forward primer comprises a first barcode at a 5' end region and the barcode reverse primer comprises a second barcode at a 5' end region; combining the sample with the at least one gene primer pair and the at least one barcode primer pair to form a mixture; and performing polynucleotide amplification reaction with the mixture, the polynucleotide amplification reaction comprising annealing between the at least one barcode primer pair and the at least one gene primer pair and between the at least one gene primer pair and the target sequence.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
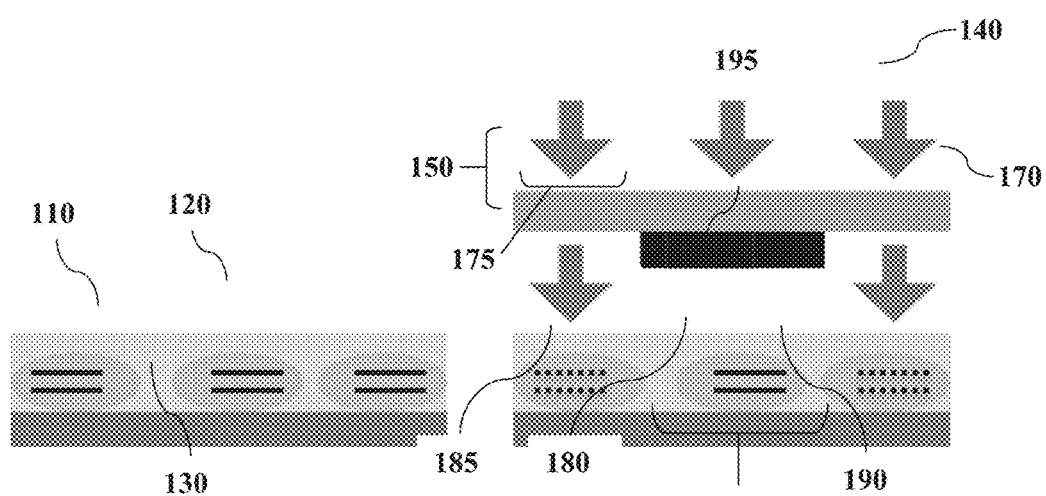
FIG. 1 shows a cross-sectional view of a series of steps in which tissue masking selectively destroys DNA.

Methods and systems are provided herein that allow in several embodiments the integration of microfluidic techniques with micro-isolation of light sensitive microscale components, such as cells and/or tissue.

The term "microfluidic" refers to a system or device for handling, processing, ejecting and/or analyzing a fluid sample including at least one channel having microscale dimensions. Microfluidic tissue isolation can be customized morphologically, functionally, and a combination of the two.

The term "micro-isolation" refers to the isolation of micro-scale components (components having a size or measure in the order of micrometers) and in particular of light sensitive microscale components, which includes, but is not necessarily limited to, one or more biological components. A biological component refers to any organized substance forming part of a living matter, e.g. a cell, cellular material, membranes, organelles, proteins, nucleic acids and/or living organisms of any dimensions or a part thereof (e.g. tissues or various cell extracts). Micro-isolation as used herein can refer to the isolation of a single nucleus, a single cell or a biological component thereof, a group of individual cells, or a cluster of cells, or a group of clusters of cells, or a specific region of a tissue or a portion thereof, or even cellular organelles (e.g. cell nuclei). In particular, in some embodiments, methods and system herein described allow one to simultaneously address a distributed group of regions of interest across a tissue slide while each region can be a single nucleus, a single cell, a cluster of cells or a biological component thereof.

In some embodiments, the proposed integration of microfluidic techniques and micro-isolation of cellular material molds the microfluidic architectures in accordance with the particular structure of each specific biological component to be isolated. In particular, in some of those embodiments, the approach described herein is mainly built around the cellular material, following the tissue structure such that the devices and methods described herein are adapted to the specific geometry of particular tissues or other biological components. By contrast, in some of the traditional approaches microfluidic devices are structured taking only in accordance with engineering considerations (e.g. path minimization, fluidic efficiency), while the biological components in applied devices are forced to comply with these engineering presets and are not taken into consideration.

In some embodiments, the subject matter described represents a paradigm shift in microfluidic technology because 1) microfluidic devices are directly integrated with, onto, or around tissue samples, in contrast to certain conventional method of off-chip sample extraction followed by sample insertion in microfluidic devices, 2) architectural and operational principles of microfluidic devices are mainly subordinated to suit specific tissue structure and needs, in contrast to certain conventional method of building devices according to fluidic function alone and without regard to tissue structure, and/or 3) sample acquisition from tissue is to be performed on-chip and is to be integrated with the diagnostic measurement within the same device, in contrast to the conventional method of off-chip sample prep and subsequent insertion into a diagnostic device.

In an embodiment, a particular sample is hardwired using photolithographically defined masks.

FIG. 1 illustrates exemplary hardwired masks. Cells (110) inside a tissue slice (120) on a tissue support (e.g. glass slide) (130) are exposed to ultraviolet (UV) light (140) through a photomask (150) comprising blocking regions (e.g. chrome regions) (160) patterned on a transparent blocking support (e.g. glass slide) (170). The blocking regions (160) are patterned in correspondence to cells of interest (180). The illuminating UV light (140) passes through a region of the transparent blocking support that is not blocked (175) and is prevented from exposing an area (195) protected by the blocking region (160). DNA in exposed cells is destroyed (185) but protected DNA inside the cells of interest is preserved (190).

The term "illumination" refers to the exposure of light. Light can be visible or non-visible light, and can be one or more of UV, two-photon, or multi-photon light or additional examples of light of various wavelength suitable to be used in connection with biological components which are identifiable by a skilled person upon reading of the present disclosure.

The term "hardwired" refers to devices, methods and systems herein described or portions thereof, that are tailored for a specific biological component of interest. For example, a particular device is hardwired if it is configured to be suitable for a specific component, e.g. a specific tissue to be investigated using methods and systems herein described. In some embodiments, hardwired devices, methods and systems are herein described that are tailored not only for a specific biological component of interest, but also for a specific investigative approach of interest. For example, in some embodiments, hardwired masks are described that allow UV light to be directed only to areas of no interest so that the DNA, protein, or other biological material in those areas is damaged to various extents and even destroyed by photodamage. In some of those embodiments, damage in areas of interest not exposed to UV is minimized to various extents and in some cases even remain intact. The term "destroy" as used in the present disclosure with reference to an item indicates a damage level able to impact at least one biological activity associated to the item. The term "intact" as used in the present disclosure with reference to an item indicates a molecule that preserve all the biological activities associated to the item.

In an embodiment, cells (or another biological components or microscale component) of interest can be identified, for example, using a microscopic computerized image of the slide and appropriate custom software, which can convert the selection into a digital image. The digital mask can be fed into a direct laser writer, e.g. Heidelberg DWL66, which transfers a digital mask onto the photosensitive material by direct writing with a resolution of 2 microns or higher (see Example 1). One skilled in the art would recognize that other laser writers or means for transferring digital masks with even higher resolution can be used with the claimed subject matter described herein.

The term "micro-isolation apparatus" refers to a device that aids in the micro-isolation of a microscale component (e.g. a biological component, which relates to biology, life and/or living processes, such as a cellular material).

The term "cellular material" refers to biological material pertaining to a biological cell. As used herein, it can refer to sub-components of a biological cell, a single intact biological cell, a group of biological cells, or a tissue.

The term "region of interest" as used herein pertains to a targeted area within cellular material. Definition of a targeted area can be of any dimensions and include one or more cellular material depending on the experimental design of choice. For example, the region of interest can be an area that is sought to be preserved, or an area that is sought to be damaged or even destroyed. In a further example, the region of interest can be as small as a DNA molecule, or as large as an entire tissue sample, a group of topologically non-contiguous targeted areas in the tissue sample, which are all to be isolated and/or extracted at a same or a different time.

The term "support" as used herein refers to any type of support in which cellular material can be mounted. One type of support is a glass slide, although one skilled in the art would recognize that many materials can provide support for cellular material.

The term "photomask" as used herein refers to the blocking support comprising a blocking region and a light accessible region. The term "blocking" refers to the ability of an item to hinder the passage of light through the item. The term "light accessible" as used herein refers to the ability of an item to allow passage of light through the item. In some embodiments, the photomask can be any type of transparent support (light accessible region) having a non-transparent region (blocking region). In some embodiments, the transparent support can further be at least in part, semi-transparent, or translucent and/or include different blocking portions with different blocking and light accessible capabilities (e.g. limited to one or more selected wavelengths for one or more areas of the photomask). In some embodiments, the photomask can be a physical object (e.g. a glass slide partially covered with chrome, or a transparency partially covered with ink or other blocking material). In some embodiments, the photomask can be purely or partially digital. For example, in some embodiments, the photomask can comprise a series of instructions to a micro-mirror array, which operates so that some mirror elements are activated while others are not. in some of those embodiments, they activate mirror elements to form a photomask pattern on a sample with respect to an illumination light reflected onto the sample by the micro-mirror array. Additional embodiments are encompassed by the present disclosure wherein a photomask is dynamic photomask, as the instructions are dynamically defined in addition or in the alternative to photomask wherein physical blocking material (e.g. chrome coating) blocks light on a suitable support (e.g. glass slide).

The term "blocking region" refers to a region of a blocking support that functions to block photons (e.g. non-transparent region blocking photons by absorption). In an embodiment, a blocked region can be a region of chrome covering the blocking support. One skilled in the art would appreciate that many metals or other materials could be used, for example, to block photon exposure. For example, titanium can be deposited on platinum, covered with a photosensitive material, and then similarly oxidized to produce a chemically and mechanically resistant oxide that can serve as a photon shield for agents damaging to microcomponents such as cellular material, such as UV exposure. In some embodiments, a material forming a blocking region can also further be a polarizer as will be understood by a skilled person.

The term "blocking support" as used herein refers to a support that can be used to support a blocking region. For example, a blocking support can be transparent, or in general configured for allowing passage of a desired lighting in one or more areas where there is no blocking region.

Embodiments of the present disclosure can use illumination light other than UV. For example, a two-photon or other multi-photon approach would use illumination of larger wavelengths where the resulting excitation would have an effective wavelength that is half or a smaller fraction of the illumination light. Such illumination wavelengths provide increased resolution because the light intensity is a strong function of the distance from the focal point, which allows more precise focusing of the illumination laser.

Hardwired masking can also be accomplished by other methods, for example, methods using polarizers and/or polarizer arrays. A polarizer surface can in principle be chemically or optically modified to produce contrast between treated and untreated regions to be used as a mask for the embodiments described herein. Some polarizers can function on the principle of aligned molecular structure of polymers, while others are based on metal wire arrays. In either case, disrupting the structural order in chosen regions, for example by heating or melting, would make such regions lose their polarizer property, which would produce the desired contrast between the regions of interest. Any hardwired method used produces a sample where the only remaining DNA and/or other biological material of interest provides the sample of interest. Thus, the destroyed and/or other biological material of interest does not contribute noise to the signal.

In an embodiment, cellular material can be micro-isolated by lamination of unwanted areas.

In an embodiment, micro-isolation by lamination provides mutual isolation of non-contiguous regions of interest, while preventing the material from contiguous or non-contiguous unwanted regions from interfering with subsequent reactions. In some of these embodiments, unwanted regions e.g. DNA or proteins of interest) can be destroyed in subsequent processing of the biological component of interest. In other embodiments, unwanted regions do not necessarily need to be damaged. In particular, in one embodiment DNA or other regions of interest (damaged or not) can be locked inside the laminate thus minimizing the possibility that contamination of the region of interest can occur. In an embodiment, a lamination approach further allows that each area of interest can be contacted with additional microfluidics for individual addressability and individual extraction. In an embodiment, the nature of the photomasking (hardwired or dynamic) is orthogonal to the choice of isolation method (e.g. DNA damaging or tissue lamination). In some of those embodiments, both photomasking methods are compatible with both isolation methods.

In an embodiment, after identifying desired cells, a suitable lithography mask can be generated to protect the contents of desired cells. In some of those embodiments, biological material such as DNA or protein from the protected cells can be used in a number of downstream applications including, but not limited to, DNA sequencing, protein analysis, etc. The purity of such specimens will greatly enhance the value and information of downstream applications. In some of these embodiments, the lamination method does not ensure destruction of unwanted biological material, but still maximizes survival of the wanted biological material, because the latter is protected by the blocked regions of the photomask, due to the requirements of the negative photoresist (see e.g. FIG. 2).

In an embodiment, the lamination-based method of micro-isolation relies on the fact that DNA and many other biological materials in tissue slice samples are neither damaged nor removed by organic solvents (e.g. ethylene, acetone, xylene). Thus, it is possible to produce a layer of photocurable material directly onto a tissue slice containing cellular material, cure in situ by photoexposure with a desirable mask pattern, and then remove the uncured sections with organic solvents without damaging the biological materials of interest. In those embodiments, photolithographic masking can thus be viewed as a way to use a photosensitive material as a microfluidic element, which can be dynamically defined by optical methods and made to match the morphology and analytical needs of the particular tissue sample.

Figure 2:
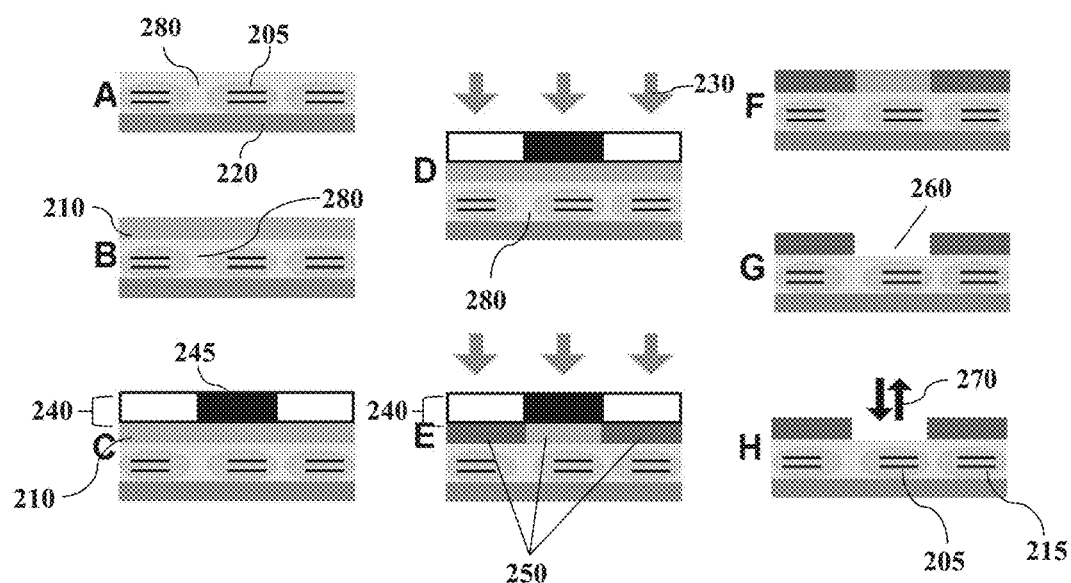
FIG. 2 shows a cross-sectional view of a series of steps where tissue isolation or masking is performed through lamination with a photosensitive material.

FIG. 2 is an example of tissue isolation by lamination. (A) A tissue (280) containing a cell of interest (205) is fixed on a tissue support (220), (13) A photosensitive material (210) is then deposited onto the tissue (280). The photosensitive material can be deposited on the tissue, e.g. by simple application, by spinning the substance down on a spincoater, by kinetic mounting, or by using spacers (e.g. microspheres of fixed dimensions) and mechanical contact with a flat surface, (C) A photomask (240) comprising a blocking region (245) is then applied onto the photosensitive material (210). (D) The tissue (280) is then exposed to UV light (230) through the photomask (240) and the photosensitive material (210). (E) Photoexposure through the photomask (240) produces a lithographic pattern (250) inside the photosensitive material (210). (F) The photomask (240) is removed. (G) A developer is applied (not shown) to remove non-cured sections of the photosensitive material, which leaves the areas of interest (260) open to interaction with the outside world. (H). The cell of interest (205) is unprotected and subjected to removal (270) for subsequent biochemical analysis e.g. extraction or in-situ measurements) whereas unwanted cells (215) are left inaccessible.

Those skilled in the art would see that the described process utilizes "negative" photosensitive materials (photosensitive material in which the protected areas are the areas that get removed), but the same technique can be applied with "positive" materials as well, by inversion of the mask.

The term "developer" as used herein refers to a chemical that reacts with a chemical (e.g. a photosensitive material) that has been exposed to light.

The term "lamination" or "to laminate" as used herein refers to the placement or layering of a material, e.g. a photosensitive material, over a sample, including but not limited to, a tissue or cell sample, and the (thermal, photo-lithographic, or otherwise) thickening or hardening of the laminating material into a "laminate," so that the biological components under the laminate are locked by it and cannot contaminate the biological components in the non-laminated areas.

The term "photosensitive material" as used herein refers to any organic soluble or water soluble material that experiences a change in solubility in a developer solution when exposed to light, such as UV light.

In an embodiment, one type of photosensitive material that can be used is photoresist. One skilled in the art would recognize that many different types of photoresist materials can be used such as negative (SU8) and positive (SPR and AZ) photoresists and additional photoresist identifiable by a skilled person. One skilled in the art would further understand that other photosensitive materials, or other photocurable polymers, can be used with the embodiments described herein. Any photo-curable material, which can include, but is not limited to, many types of polymer, elastomer, or epoxy, can be used as a negative photosensitive material. Any substance that becomes soluble after UV exposure can act as a positive photosensitive material, for example, urethane or Polymethylmethacrilate (PMMA) and additional materials identifiable by a skilled person.

The use of a negative photosensitive material is shown in FIG. 2. The "dark" areas of the mask are designed or programmed to allow access to the protected areas once the developer is applied because negative photoresists use organic solvent developers, which neither damage nor extract DNA and RNA during the development process, because the DNA and RNA are charged and hydrophilic. Subsequently, the DNA and RNA can be extracted or analyzed in situ in aqueous solutions.

The use of positive photosensitive materials causes the UV-exposed photosensitive material to be soluble in developer, such as an aqueous alkaline developer, so that areas not protected by the mask would be open to interaction (not shown). This allows hydrophobic molecules (e.g. hydrophobic lipid-soluble proteins) to be extracted by organic solvents that do not damage the positive photoresist coating of the unwanted areas.

One skilled in the art would recognize that DNA and other biological material can be damaged by UV light. Nonetheless, one skilled in the art would also recognize that DNA most strongly absorbs light with a wavelength below about 320 nm, while many photosensitive materials are activated at higher wavelengths, for example, at 400 nm. Although some light processing systems use a wide wavelength range, it can be appreciated that cut-off filters or other means that are commonly known can be used to limit the excitation light to wavelengths that are too long to damage DNA but are short enough to expose the photoresist, which can include, but is not limited to, wavelengths between about 350 nm and about 400 nm as will be understood by a skilled person.

Photoexposure can occur by any means known in the art, which includes, but is not limited to, UV exposure, light emitting diodes, or photonic crystal devices, or alternatively or in addition, reflected onto the sample by micro-mirror arrays.

Figure 3:
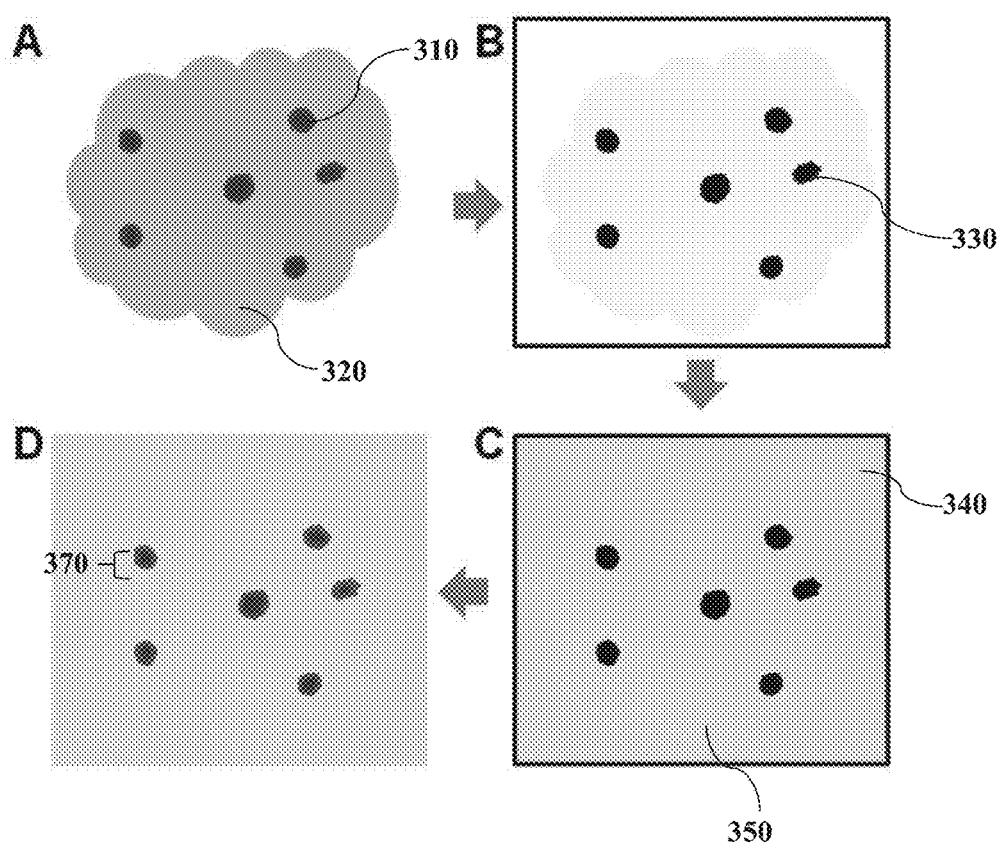
FIG. 3 shows a top view of an embodiment in which tissue isolation targets multiple areas of interest occurring by lamination with a photosensitive material.

FIG. 3 shows from a top view the same process of tissue isolation by lamination as FIG. 2. (A) Clusters (310) of potential cancer cells within a tissue sample (320) are selected. The clusters provide a plurality of cells, each of which are targeted in a manner described in FIG. 2. (B) The selection is reflected in a photomask (either hardwired or dynamically defined) of black spots (330). (C) A photosensitive material (340) is deposited onto the tissue sample (320) and a tissue support (not shown); the photomask (330) is aligned on top, and UV light (not shown) is directed through the photomask (330) to expose the photosensitive material (340) over unprotected unwanted regions. (350) (D) The tissue slide (not shown) is treated (e.g. with a developer), which removes unexposed photosensitive material above the areas of interest. Defined access wells (370) in the photosensitive material (340) ensure that only the wanted areas can be extracted with suitable methods (e.g. chemically) for further analysis.

The term "well" or "wells" or "access wells" or "defined access wells" as used herein describes an area around a tissue region of interest that provides access to that particular region of interest.

In an embodiment, the tissue lamination approach is coupled with microfluidic devices placed on top of the photosensitive material in order to individually analyze regions of interest.

A photolithographically masked tissue containing cellular material can be integrated with a microfluidic chip (e.g. consisting of a series of chambers matching the mask) which can be fabricated in situ or separately. The chip can be used to extract the subsamples of the selected area. The chip can also be used to supply reagents for in-situ analysis (e.g. immunoassay, PCR, RT-PCR), which allows unequaled flexibility and parallelism in the microfluidic dynamic selection of tissue areas of interest for each individual slide.

Figure 4:
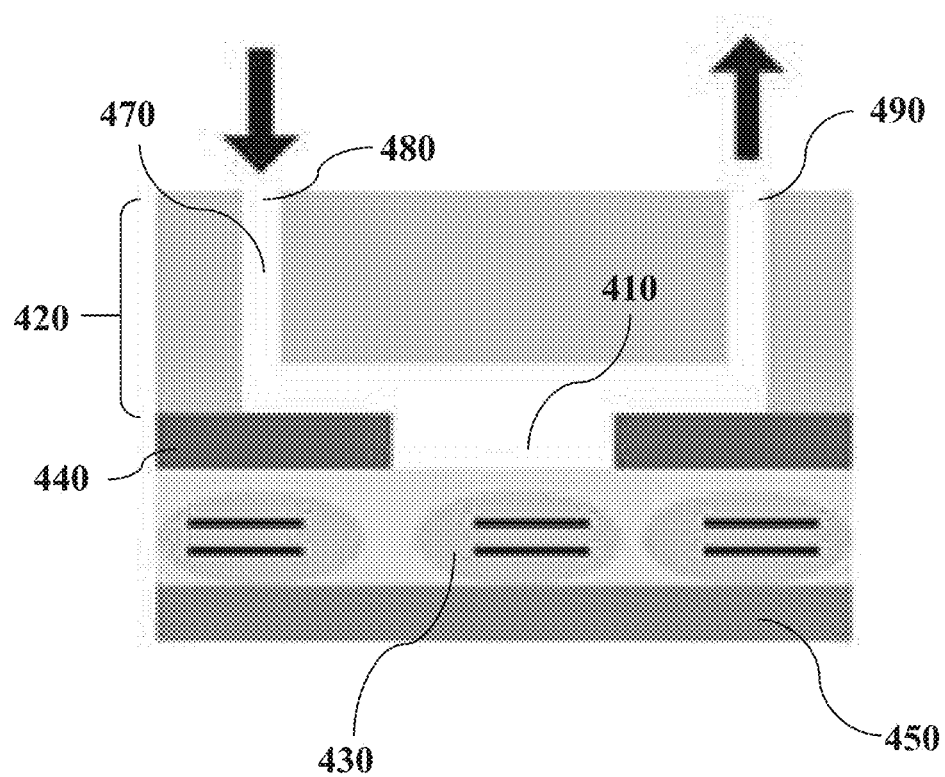
FIG. 4 shows a cross sectional view where a tissue is integrated with microfluidic elements.

As shown in FIG. 4, access wells (410) defined in a photosensitive material (440) over cells of interest (430) placed on a tissue support (450) can be accessed microfluidically by producing and aligning a chambered microfluidic device a microfluidic chip) (420) comprising channels (470) having an input (480) and an output (490).

In some embodiments, the overlay can be made of silicone, silicon, or glass.

As described herein, the term "microfluidic chip" or "chip" as used herein refers to least one substrate having microfluidic structures contained therein or thereon. For example in an embodiment, the chips can be one-layer, e.g. made of silicone, where horizontal channels are confined in a single 2-D plane, with vertical channels only for input/output operations. The chips can also be multi-layer devices [ref. 2], where each layer of the material contains its own network of channels. Such networks can be connected with vertical connecting channels called "vias" [ref. 3]. The chip can contain valves, or a plurality of valves and arrays of valves. One skilled in the art would appreciate that any chip that can be integrated with microfluidic wells defined in photosensitive material to allow for highly specific extraction of desired cells can be used.

The term "channel" or "channels" or "chamber" or "chambers" as used herein refers to a pathway formed in or through a medium that allows for the movement of fluids, such as liquids and gases. The term "input" or "inputs" as defined herein is intended to refer to areas of the microfluidic device where materials (e.g. proteolysis agents, gases, other liquids) can be introduced through the chambers to the regions of interest. The inputs further allow introduction of materials to multiple areas of interest through channels connected to the chambers.

In various embodiments, a chip herein described can provide a multitude of analytical functions. The term "analyze" and "analytical" refer to activities related to process of the microscale component at issue for the purpose of detecting information related to the component. For example, in embodiments where the microscale component is formed by biological material, analytical functions comprise activities directed to process the biological material to identify information concerning and/or originating from the material which are identifiable by a skilled person. For example, in an embodiment, the integrated chip can uptake micro-isolated cells, lyse such cells, capture DNA, RNA, and/or other biological materials by specific or general hybridization assays to magnetic nanoparticles, which can then be extracted from the chip for traditional PCR analysis off-chip. In an embodiment, the chip can also uptake the micro-isolated cells, lyse such cells, and perform PCR on-chip. In some of those embodiments, on-chip PCR allows subsequent detection of specific genes or mutations by molecular beacons or on-chip specific hybridization arrays. In an embodiment, the chip can also uptake a biological components such as micro-isolated cells, lyse such cells, and then perform immunoassays on intracellular proteins, e.g. for proteomics-level expression analysis. In an embodiment, the chip can also be used to extract the cell regions micro-isolated by the lamination techniques described herein, separate the clusters into single cells, then feed each cell into a single-cell analysis device, e.g. for DNA sequencing, mutation detection, or gene expression analysis. Such devices as the enumerated examples can be used in fundamental research, and can also be adapted as biomedical diagnostic tools, e.g. in oncology and pathology. Additional variations of these devices, wherein same or further functionalities are added or combined are encompassed by the present disclosure as would be understood by a skilled person.

The term 'output" or "outputs" as defined herein is intended to refer to areas where the cellular material from the regions of interest can be extracted for further analysis. Input/output operations can be conducted by microfluidics, thus preventing contamination, waiting for diffusion, and excessive dilution of the sample. Also, the chip itself can have analytical function, e.g. microfluidic immunoassays or microfluidic PCR and RT-PCR.

In some embodiments, the described integration of tissue lamination micro-isolation with microfluidic devices allows the leveraging of the advantages of microfluidic handling (e.g. micro scale, fast diffusion, parallelism, integrated mechanical and/or chemical functionalities) with the advantages of the described micro-isolation technique (e.g. high specificity, parallelism, low cost, flexibility, and/or dynamic masking). In some of those embodiments, this architecture provides flexible sample-specific interface between the unique patterns of the particular sample morphology and the hardwired architectures of conventional microfluidic devices.

Figure 5A:
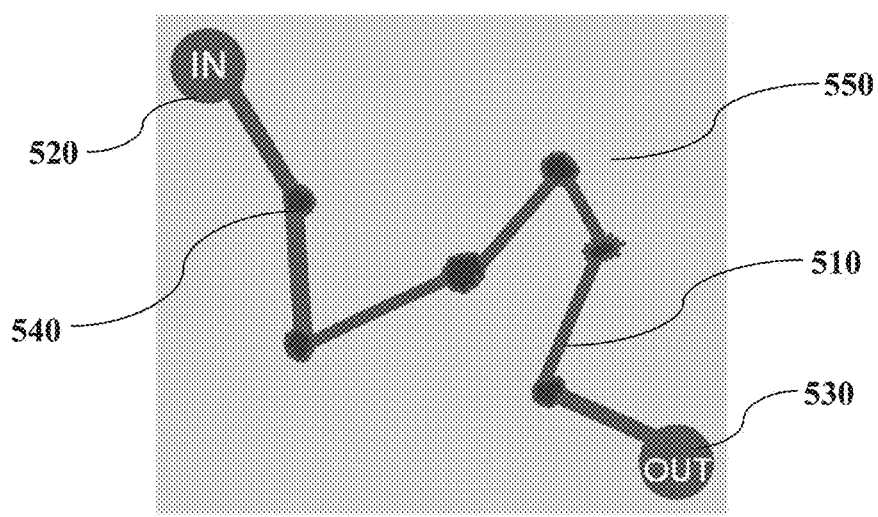
FIG. 5A is related to FIG. 3, and illustrates a top view of a customized chambered microfluidic device.

FIG. 5A shows a top view demonstrating a hardwired multi-chambered approach wherein regions of interest (from FIG. 3) are connected via channels. A laminated tissue sample (550) is integrated with a chambered microfluidic device (as shown in FIG. 4), whose channels (510) connect to chambers (as described in FIG. 4) over the laminated tissue's cellular areas of interest (540). An input (520) allows introduction of components necessary to collect extracts into a single output (530). FIG. 5A shows a single input and output, although multiple inputs and outputs are possible. In this particular approach, the entire chip is customized to the extraction needs of the particular sample, although as described herein, multiple approaches are possible.

Figure 5B:
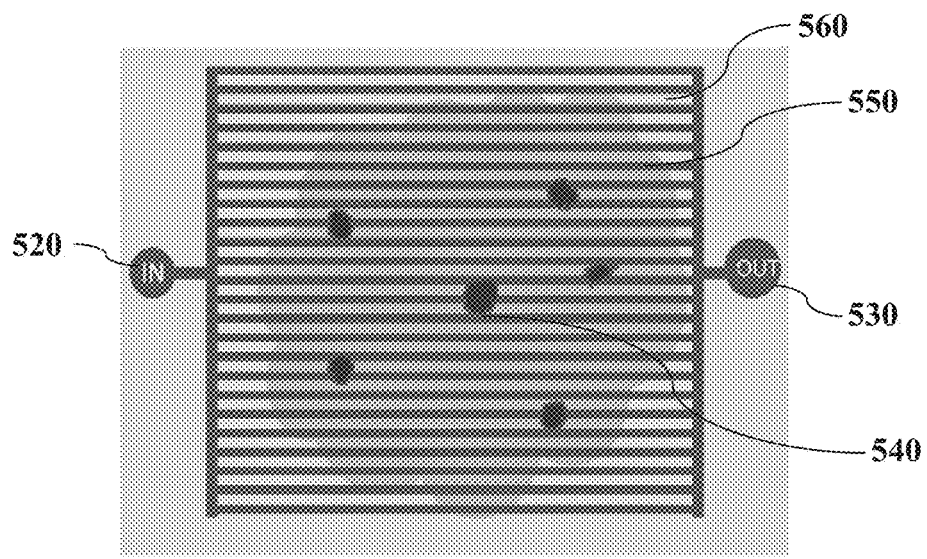
FIG. 5B is related to FIG. 3, and illustrates a top view of a standardized chambered microfluidic device.

In an embodiment, the lamination is customized to the particular sample, but the rest of the microfluidic device can be standardized and thus used universally with any and all tissue samples. As used herein, a universal microfluidic device is a device that can be standardized and used with multiple tissue samples that have been selectively or non-selectively isolated. For example FIG. 5B shows a top view demonstrating a standardized multi-chambered approach. In this approach, a laminated tissue (550) is integrated with a chambered microfluidic device (as shown in FIG. 4), whose standardized matrix of channels (560) connect to chambers (as described in FIG. 4) over the laminated tissue's cellular areas of interest (540). An input (520) allows introduction of components necessary to collect extracts into a single output (530). FIG. 5B shows a single input and output, although multiple inputs and outputs are possible. Those skilled in the art would appreciated that a standardized multi-chambered chip can be configured in one of many possible ways in order to allow microfluidic channels to cover a tissue surface adequately in order to extract desired cells from randomly distributed locations. For example, the grid can be rectangular as shown in FIG. 5B, or a binary tree of parallel channels. In addition, a universal extractor device can be combined with a sample-specific micro-isolation technique. In embodiments, wherein the spacing in a grid or mesh of channels is not bigger than the expected size of wanted clusters, a fluidic connection between one or more wanted cluster with at least one of the extraction channels can be performed. Thus in some of those embodiments a universal extractor device can be combined with a sample-specific micro-isolation technique (e.g. the described lamination method). In some embodiments, in particular the described combination can have the benefits of both techniques in the same system—low cost and universal applicability offered by the standardized chip with the high specificity and sample-specific customization of the micro-isolation technique.

In an embodiment, a tissue is completely encapsulated inside a microfluidic device, to allow for full surface access.

Tissue encapsulation captures a tissue of interest between two separate microfluidic devices, which allow simultaneous access to two surfaces. If the slice is sufficiently thin, fluidic communication is ensured through the slice. Such communication allows more efficient and reliable extraction of desired samples, as a resuspension liquid can be used to push desired material out of the tissue matrix. This approach allows extraction of desired material by microfluidic/hydraulic means without the need for more aggressive chemical treatments.

Figure 6:
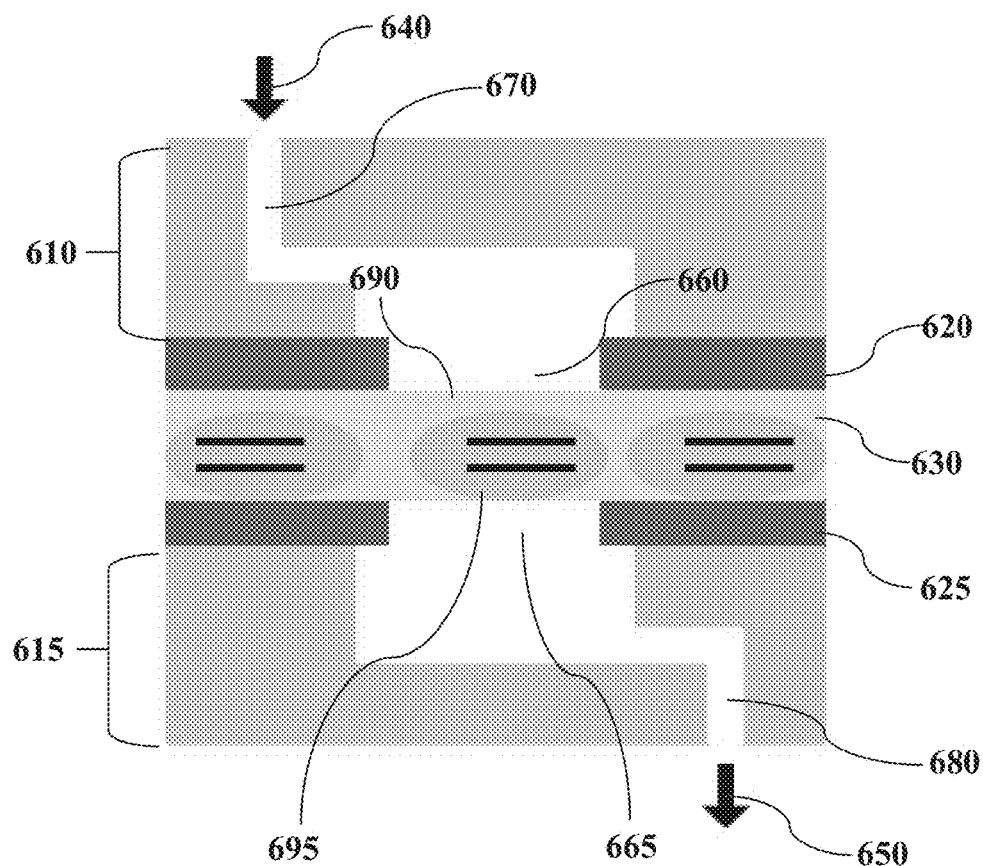
FIG. 6 shows a cross-sectional view of an embodiment where tissue encapsulation is performed.

FIG. 6 illustrates an embodiment where complete encapsulation is shown. A tissue slice (630) covered in a photosensitive material both above (620) and below (625) the tissue slice and defined by access wells both above (660) and below (665) the tissue slice that can be integrated with microfluidic devices (e.g. microfluidic chips) positioned above (610) and below (615) the cells of interest and having chambers from both above (670) and below (680) the tissue slice. This architecture allows a more efficient input (640) and output (650), while an area of contact (690) can be doubled for better access to the cells of interest (695).

In an embodiment, tissue encapsulation allows the use of 3D polymerization for in-situ chip construction around the 3D tissue sample. This can be done, e.g. by using direct laser writing and 3D rastering to build the desired architectures such that the monomer material for the chip can be spread thick over the tissue sample. The laser can then polymerize the chip material in the desired shape over the tissue sample. The tissue is completely submerged in a monomer, while a 3D chip is built around it, thus allowing microfluidic access to the sample from all directions. In some embodiments, performed according to this approach, the photocurable polymer of the chip material itself can be used as a photosensitive material, wherein a tissue slice can be placed inside the polymer prior to 3-D photopatterning (e.g. before a 3-D) photopatterning commences)

In an embodiment, multiple areas of interest are addressed with individual channels without masking.

Individually and collectively controlled arrays of microvalves, which allow the same architecture to address a customizable subset of chambers of access loci within the matrix, can provide the ability to match particular regions of interest on the particular tissue sample. A chip with a dense pore matrix allows the differential opening of particular pores for a short time such that only material confluent with the pore would flow from the sample into the chip for analysis without masking.

Figure 7:
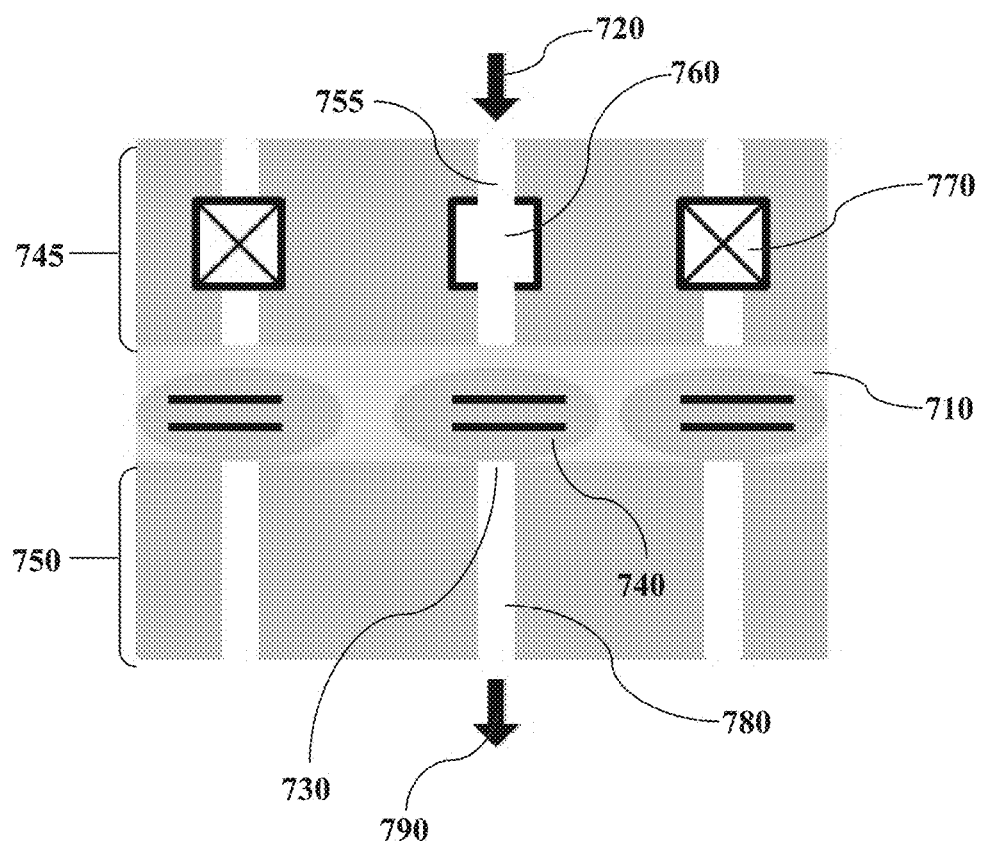
FIG. 7 illustrates an embodiment in which a maskless chambered microfluidic device encapsulates the tissue encapsulates a tissue without customized photomasking while specificity of micro-isolation is achieved through active control of arrays of valves allowing specificity of micro-isolation to be achieved through active control of arrays of valves.

Maskless microfluidic encapsulation is shown in FIG. 7. A tissue slice (710) is encapsulated in a dense pore matrix microfluidic device both above (745) and below (750) the tissue. Individually addressable valves that are closed are shown marked with an "X" (770) as opposed to valves that are open (760) to allow flow through the open channel (755). The open valve (760) forces a pressure drop that ensures input flow (720) and forces material from a cell (740) through a pore (730) into an output channel (780) and through an output (790) for analysis.

An embodiment provides tissue micro-isolation by microfluidic matrices for parallel analysis of subsamples with preserved morphological context.

According to an embodiment, microfluidic matrices with highly parallel single-cell analysis is based on the combination of a nanofabricated microfluidic matrix and a tissue section. This allows a matrix of millions of microfluidic wells to be filled with biochemical reagents and contacted to a tissue section deposited on a support. For example, each well can contain Proteinase K and sequencing reagents. The Proteinase K digests the tissue and releases the contents of each cell into its adjoining well, where they mix with the PCR reagents by diffusion. The entire system is contacted to a thermally controlled aluminum plate, to perform standard or isothermal PCR. Mutant genes can be amplified by appropriate selection of primers and reported by fluorescent probes. Signal detection is done by scanning the entire slide on a fluorescence scanner or by fluorescence microscopy performed one sector at a time followed by digital assembly. The result is a highly parallelized single-cell (genetic) analysis of the entire tissue.

Figure 8:
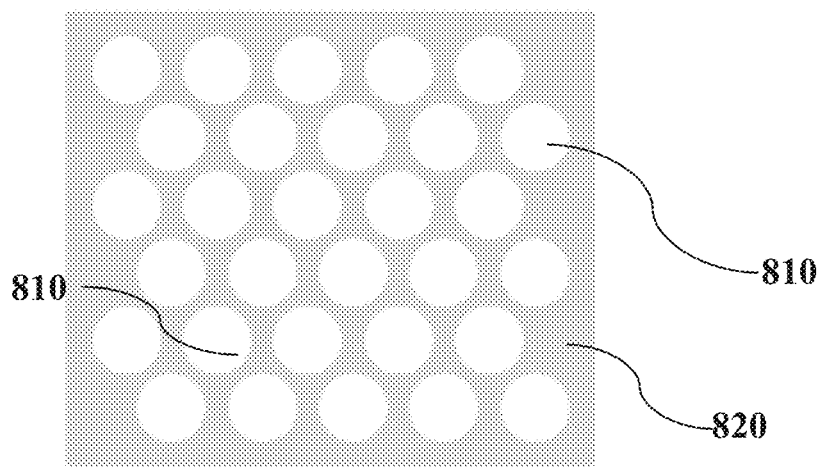
FIG. 8 illustrates a top view of a matrix of microfluidic

An exemplary matrix of microfluidic wells according to an embodiment herein described is illustrated in FIG. 8, which shows a top view of access wells (810) inside a matrix (820) (built in e.g. glass silicon, or silicon-on-insulator). Access wells (810) can be defined, for example, by spreading a photoreactive material on a substrate, exposing the photoreactive material to UV light through a photomask, developing the photoreactive material, and etching the exposed areas. Following removal of the photoreactive material, the result is defined access wells in the substrate with the same geometry as the photomask. The term "dense-pore matrix" as used herein refers to a matrix having dense pores.

Figure 9:
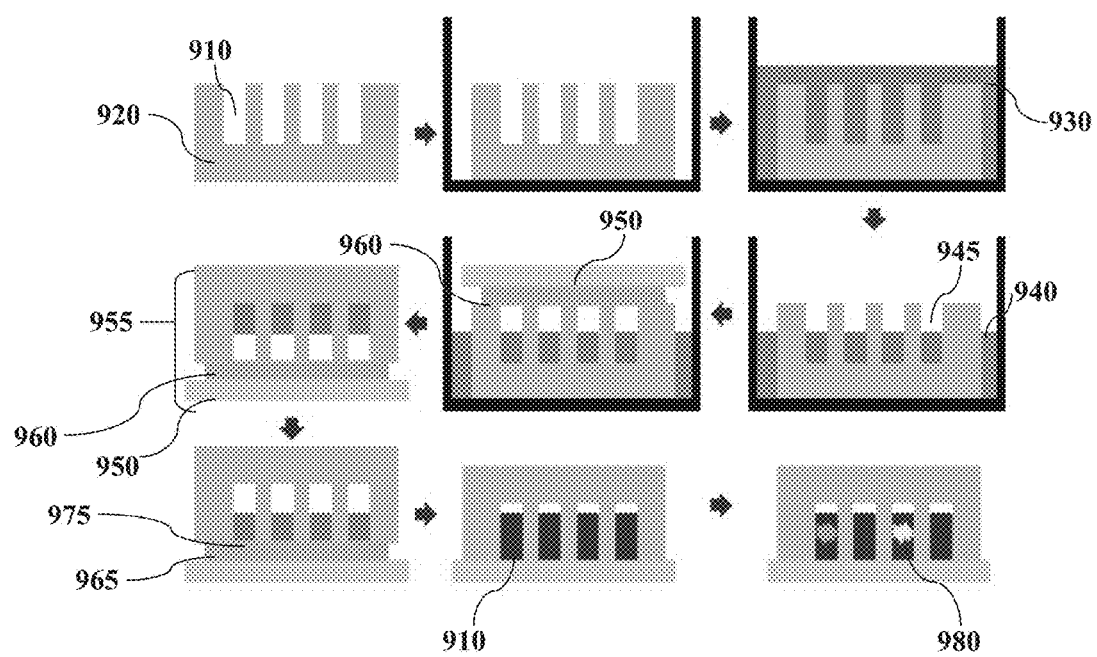
FIG. 9 shows a series of steps for the parallel processing of isolated tissue subsections.

FIG. 9 shows an exemplary illustration of how a matrix of microfluidic wells can provide access to individual cell nuclei for independent reactions. Microfluidic access wells (910) are defined in a substrate (920) (e.g. glass or silicon). Next, the access wells (910) are filled with a fluid mixture (930) containing digestion and reaction agents (e.g. Polymerase Chain Reaction (PCR) reagents, and fluorescent probes). Next, evaporation is performed to uniformly decrease the fluid mixture level (940), leaving space at the top (945) of the microfluidic access wells. Next, a tissue support (950) is aligned on top with a tissue slice (960) facing downward. Next, an assembled construct (955) is clamped together and vertically turned over, allowing the fluid mixture to flow by gravity and cover (975) the tissue. Next, the digestion agents contained in the fluid mixture break down the tissue (965), releasing the cellular contents into the microfluidic access wells (910). The reaction reagents within the fluid mixture complete the reactions and fluorescent probes (980) reveal results.

In an embodiment, releasing the cellular content of the tissue can be performed by digestion of the tissue performed using Proteinase K. or other techniques of chemical digestion such as the ones described in [ref. 4,5] which allow multiple analysis of different molecules in the cellular component. For example, in an embodiment techniques can be used that allow immunoassay analysis of the extracts as well as DNA and protein analysis at various scales as it will be understandable by a skilled person.

Figure 10:
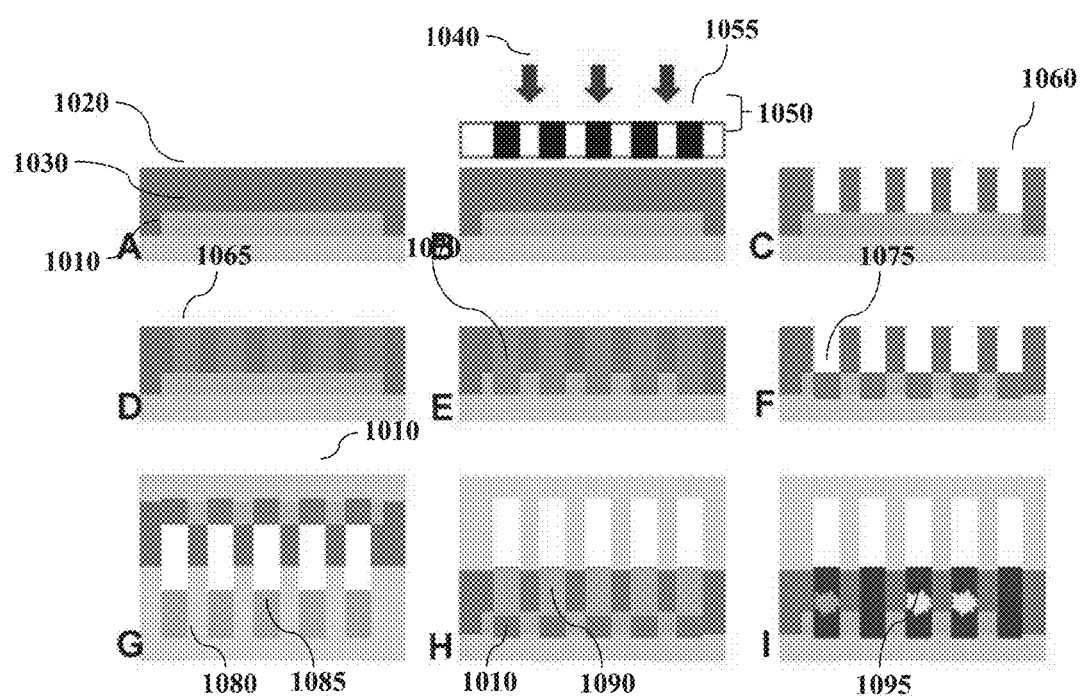
FIG. 10 shows a series of steps for the parallel processing of isolated tissue subsections that allows step-wise administration of biochemical agents.

In several embodiments, the nanomatrix technique herein described can be modified in view of the specific reagents, biological component, desired result and experimental design as will be understood by a skilled person. For example, in an embodiment, a matrix of microfluidic wells can provide access to individual cell nuclei where a two-step process allows separate biochemical reactions to occur. By way of example, FIG. 10 shows a process in which cells can be digested with Proteinase K prior to a PCR reaction. In the illustration of FIG. 10 tissue (1030) is placed atop of a support (1010) and a photosensitive material (e.g. negative photoresist) (1020) covers the tissue (Panel A). Next, a photomask (1050) having—blocking regions (1055) is placed over the photosensitive material and exposed to UV light (1040) (Panel B). Next, the photomask is removed and an organic solvent developer removes the photosensitive material from the unprotected areas, leaving defined access wells (1060) (Panel C). The defined access wells are filled with solution containing Proteinase K (1065) (Panel D), which digests exposed tissue (1070) and releases the DNA into the solution in each well (Panel E). Heating deactivates the Proteinase K and lyophilizes DNA in place in each respective well (1075) (Panel F). Next, a corresponding matrix of wells is etched in a well support (e.g. silicon, glass, or silicon-on-insulator) (1080), which is filled a solution containing PCR reagents (1085) (Panel G). The assembly is then mechanically secured together (e.g. clamped) providing water-tightness between compartments, and then turned over, allowing the PCR solution to resuspend the lyophilate within each well (1090) (Panel H). PCR can proceed simultaneously yet separately, in which fluorescent probes (1095) reveal results of the reaction (see starbursts Panel I). Data acquisition can be performed e.g. on a fluorescence scanner or by an optical fluorescence microscope, where the wells are optically accessed by the side of the glass slide in panel I.

In the embodiment exemplified in FIG. 10, when the surface density and size of the wells are correctly chosen, most wells will adjoin one and only one cell. In some embodiments, wherein the biological component is formed by cells, an expected optimal well size is about the same as the size of a mammalian cell (~20 µm). However, in those embodiments, one skilled in the art would recognize that the size and spacing of the wells can be optimized to ensure that the overwhelming majority of wells contain just one cell. This would maximize purity of the sample in each well, and thus maximize specificity and reduce noise in an analytical determination.

In an embodiment, a maskless microisolation apparatus methods and systems are described that are configured according to the microscale component of interest and experimental design and do not require (although they could include) photomasks and/or photosensitive material. For example, in some of those embodiments, a maskless microisolation apparatus can have randomly placed access wells that are configured relative to the biological material of interest and the experimental design. In particular, in embodiments where the biological material is comprises cells and the experimental design is directed to isolate and/or analyze individual cells, a dense porous "honeycomb" arrangement of predetermined access wells can be used in a device, methods or systems herein described such that the pre-existing access wells can be placed accordingly over cellular regions according to the specific analysis of choice (e.g. to perform protein and/or DNA analysis of regions of interest selected).

In some embodiments, the configuration of a matrix of access wells herein described is not limited to desirable areas alone. In some of those embodiments, some or all wells can be analyzed simultaneously but separately, so that no predetermined regions are necessary. Accordingly, in an embodiment, of devices methods and systems herein described a photomask can be designed to single out only the areas of interest and/or to include a repeating regular or irregular geometric pattern of choice (e.g. circles, squares, or hexagons in rectangular, checkered, or honeycomb formation) of appropriately chosen size and spacing, e.g. to contain only one microscale component or portion thereof (e.g. one cell per well).

In several embodiments, wells of a masked or maskless matrix of access can include one or more reaction mixtures. A reaction mixture can be any mixture containing components necessary for a biochemical reaction to occur. Reaction mixtures can include, but are not limited to, components necessary for PCR, real-time PCR, RT-PCR, flow cytometry, fluorescent labeling, FRET, DNA sequencing, protein-protein interaction assays, immunoassays, protein-nucleic acid assays, and any other biological reaction known in the art.

A matrix of microfluidic wells allows incomparable parallelism in extracting the sequencing information while preserving the morphological and contextual information from the tissue sample. It enables large-scale mapping of two-dimensional spatial distribution of mutations across a tumor section. If such maps are made of consecutive sections of the same tumor, a three-dimensional distribution of mutations within a tumor can be digitally assembled. Furthermore, such 3D maps can be generated for analogous tumors in multiple test animals at different temporal points of tumor evolution. Thus, the temporal evolution of a 3D distribution of mutations can be assembled.

In many embodiments, the optimal well size is the same size as a mammalian cell (approximately 20 µm), although one skilled in the art will recognize that different well sizes can be used for different applications.

Figure 11:
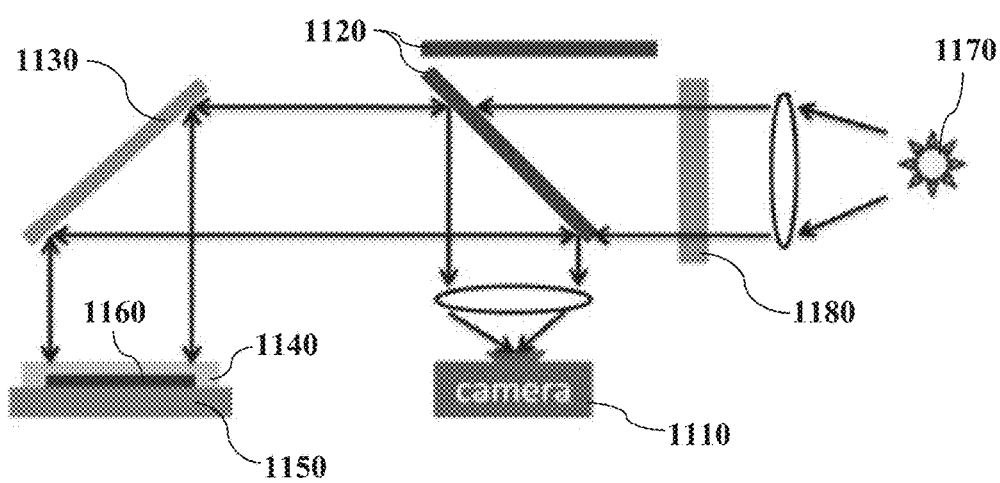
FIG. 11 illustrates an optical setup for dynamic optical array masking.

In an embodiment, an active array of masking material replaces a physical mask with micro-mirror arrays. As illustrated in FIG. 11, which is a dynamic process allows the targeted positioning of tissue selection. First, cells and/or tissue (1160) are shown to an operator and a camera (1110) takes an image of cells and/or tissue through an adjustable mirror (1120), a Digital Light Processing (DLP) mirror (1130) and a photosensitive material (1140). The image shows the cells and/or tissue (1160) placed on a tissue support (1150). Upon observation of the image, an area of interest is selected by programmable patterning the DLP mirror (1130). Second, the adjustable mirror (1120) is adapted to be positioned accordingly so that UV light from a lamp (1170) can be directed through a long-pass filter (1180) and through the programmed DLP mirror (1130) onto the photosensitive material (1140) and directed to destroy the DNA of the cells in the region of interest (1160).

A long-pass filter indicates a device that operates to allow all light coming from the UV light having a wavelength above a certain value, e.g. about 350 nm. Long-pass filters are standard optical elements known to people skilled in the art. The particular long-pass filter suitable for the embodiment exemplified in FIG. 11 is configured to ensure that virtually all light coming from the illumination source has a wavelength above the cut-off value of about 350 nm. The usual structure of long pass filters is a Bragg stack of layers of dielectric materials with carefully controlled thicknesses. The thickness and refractive index of each layer sets up destructive interference for a narrow band of wavelengths that are meant to be stopped. Making a stack of such layers ensures that a wider cumulative range of wavelengths is stopped by the filter. In this particular case, the cut-off value is 350 nm, because wavelengths above it are too long to damage DNA when DNA is chosen as microscale component of interest, but short enough to expose the photoresist correctly. In the exemplary system of FIG. 11 the long pass filter is for the tissue lamination method, which necessitates the exposure of the photoresist which becomes the laminate. People skilled in the art (e.g. optics and engineering) understand all the possible variations of long-pass filters in devices, methods and filters herein described.

The term "digital image" refers to an image generated by a computer or other suitable electronic device. In an embodiment, a digital image can be provided, for example, by a set of instructions in software on a computer controlling the optical hardware. In an embodiment, the image can be a 2-D image. In an embodiment, the digital image can also be 3-D, e.g. in embodiments, when a device is provided for tissue encapsulation by 3-D rastering of the photocuring illumination, as described herein. A "digital mask" refers to the masking of a region of interest of cellular material based on a digital image as opposed to a physical mask, e.g. a chrome mask.

In an embodiment, tissues can be micro-isolated without the need for a physical mask for UV shielding. Instead, a UV laser, e.g. Heidelberg DWL66®, can be focused directly onto the necessary spots in the photoresist on top of the tissue for lamination or in the tissue itself for destruction of biological material in the tissue such as DNA. The resolution can be 2 microns or better, and the desired cells can be skipped in the rastering process. Different laser heads can be used for the different regions of the slide. For example, appropriate software can guide the laser with a 2-micron head around the immediate vicinity of the cells of interest, while the rest of the slide area is exposed by broader strokes, e.g. with a 30-micron head.

In an embodiment, active masking arrays utilize LCDs (liquid crystal displays). An illumination light would be polarized along one axis, while the LCD elements would be polarized along one axis to disallow and another axis to allow the passage of the UV light. The cells of interest are protected by having the corresponding elements in the array be perpendicularly aligned, while the unwanted cells would have their elements aligned in parallel with incident UV illumination.

In an embodiment, dynamic masking using fiber optics can be produced by arrays of LEDs (light emitting diodes). This approach allows the utilization of increasing smaller wavelengths as current technology builds LEDs at smaller wavelengths. Individually addressable elements can be built at the microscale, producing macro-sized arrays of thousands or millions of individually addressable LED elements. Such individually addressable LED elements allow respective areas on the photosensitive material to be individually photopolymerized to provide the tissue lamination methods described herein.

In an embodiment, fiber optics is used in a way similar to intensified CCD cameras. Bundles of fiber optic cables are arranged to produce an active array of illuminators. This bundle can be coupled to an LCD array at the input of illumination light, while the output is coupled to the tissue slide. Then the output size of each fiber can be made smaller than the input size, producing both light transduction and size reduction.

In an embodiment, active masking array uses photonic circuitry to define dynamic optical arrays. A photonic circuit can in principle be built to generate an array of individually addressable optical outputs. When positioned over a tissue slide, the individual addressability of optical outputs provides the capability for individual UV exposure of tissue areas that are chosen to be discarded.

In an embodiment, active masking array uses photonic circuitry to define dynamic optical arrays. A photonic circuit can in principle be built to generate an array of individually addressable optical outputs. When positioned over a tissue slide, the individual addressability of optical outputs provides the capability for individual UV exposure of tissue areas that are chosen to be discarded.

In an embodiment, active masking array uses micro- and nano-lasers for dynamic arrays. These lasers can be fabricated in arrays, where each laser is still individually addressable. Software and electrical outputs control which laser is active, e.g. by electrical pumping or electrical control of polarization shielding against pumping illumination. Microfluidic devices can further follow a combination of morphological and functional customization. For example, in the particular technique of multi-layer elastomer microfluidics, the elastomeric layer that contacts the sample can have a photolithographically defined morphology that matches the regions of interest in the tissue sample, while other layers can follow a matrix or array structure built for functional programmability As an example, see FIG. 5A, where a uniform matrix of channels overlays the wells of the regions of interest, ensuring extraction. Thus the extraction matrix can be standardized and thus produced inexpensively, while the laminating layer is kept specific to the particular tissue sample. One skilled in the art would appreciate that such a combination is clearly not limited to extraction alone, because a device of any processing or analytical function can be integrated with a sample-specific micro-isolation stage. In some embodiments, the specific functionality or purpose of the device can be combined with the high specificity and sample-specific customization offered by the described micro-isolation techniques. In some of those embodiments, this approach provides a low cost of standardization with a high specificity of sample-specific extraction In some embodiments, the methods and devices described herein overcome various problems e.g. by providing a general microfluidic bottoms-up sample-specific customization method. Such a method naturally leads to rapid, parallelized, and highly specific micro-isolation of the desired cell subpopulation (e.g. cancer cells from a tumor) directly from tissue samples. In particular, in some embodiments, devices, methods and systems herein described preserve the structural integrity of most of the tissue, thus preserving its inherent morphological information. In some embodiments, a PCR nanomatrix technique is described that allows parallelized large-scale high-throughput genomic mappings across the tissue sample.

In several embodiments, methods herein described allow convenient application in a number of methods to separate normal from cancer cells (See Ref. 1). Methods herein described are not necessarily dependent on use of fresh tissues, and are applicable to most human cancer specimens, which are usually fixed in formalin and paraffin-embedded. In some embodiments, devices methods and systems herein described allow to process wanted cells (e.g. cancer cells) minimizing the background noise of unwanted cells (e.g. non cancerous cells). In some of those embodiments, devices, methods and systems herein described allow a less expensive and less labor-intensive of certain methods of the art where a trained operator must manually identify and then individually address each cell to be analyzed using an expensive and complex laser microscopy system.

In some embodiments, devices, methods and systems herein described can be performed in microfluidics. In particular, in certain embodiments, microfluidics is the micro-manipulation of fluids, and can be integrated with biochemical applications for microscale analyses of cells with further implementation identifiable by a skilled person.

In several embodiments, devices methods and systems herein described are configured to combine sample specific microisolation with standardized processing and/or analysis chip. Microisolation can be used to control and in particular increases up to maximize specificity of selection. Use of a standardized processing and/or analysis chip can provide an economic and industry friendly way to materialize the technique in practice.

According to several embodiments, microisolation devices methods and systems are described wherein: cellular material or other microscale component is positioned on a substrate; a sample specific micro isolation method herein described is applied to the cellular material or other component to obtain a substrate presenting the cellular material, a microfluidic universal device is connected with or contacted to the substrate presenting the cellular material, the universal device being analysis specific and sample non specific; and a microisolation methods is used to extract the material from the desired regions on the particular sample and the universal device is used to collect and/or analyze the extracted sample Although any methods and materials similar or equivalent to those described herein can be used in the practice for testing of the products, methods and system of the present disclosure, exemplary appropriate materials and methods are described herein as examples.

EXAMPLES

The devices, methods and systems herein described are further illustrated in the following examples, which are provided by way of illustration and are not intended to be limiting.

In particular, the following examples illustrate exemplary hardwired and laminated devices and related methods and systems. A person skilled in the art will appreciate the applicability and the necessary modifications to adapt the features described in detail in the present section, to additional solutions, devices, arrangements, methods and systems according to embodiments of the present disclosure.

Example 1

Hardwired Masking Using Photolithographically Defined Chrome Masks

Cells of interest are identified using a microscopic computerized image of the tissue slide and appropriate custom software, which converts the selection into a digital image. The digital mask is fed into a direct laser writer, the Heidelberg DWL66®, which transfers a digital mask onto the "positive" photosensitive material deposited on top of a chrome-covered plate, by direct writing with a resolution of 2 microns. The plate is then developed to remove the exposed photoresist, which leaves the exposed areas susceptible to chemical etching. The etching removes the unprotected chrome, and the rest of the photosensitive material is removed, e.g. by overdevelopment or exposure to a strongly alkaline solution. The remaining chrome pattern is quickly oxidized by atmospheric exposure, typically within 30 sec, which produces a chrome mask specific to the particular tissue sample. An exemplary hardwired masking using photolithographically defined chrome masks is illustrated in FIG. 1.

Example 2

Application of Tissue Lamination Approach to Adrenal Gland Tissue Slides

The tissue lamination technique was applied to adrenal gland tissue slides prepared by routine clinical methods. Photoresist SUS-2005 was deposited onto a tissue by spinning the slide on a WS-400B-6NNP/LITE spincoater. The slide was pre-baked at 65° C. Next, the slide was exposed to UV filtered with a 368-nm high-pass filter at an MA-6 mask aligner, through a chrome-on-glass mask bearing the pattern of a USAF 1951 resolution chart. The chart was chosen as a mask to provide an easily identifiable reference in terms of size of the defined features in photoresist on top of the tissue.

Figure 12:
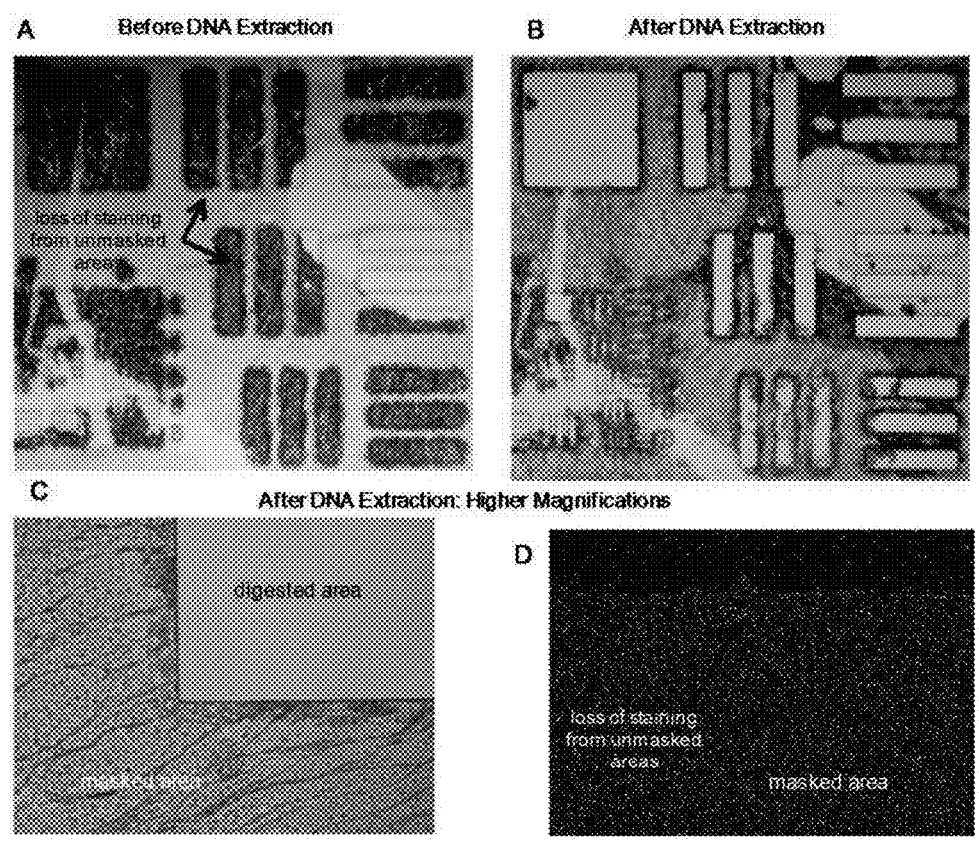
FIG. 12 provides optical microscope optical microscope images as an Example of the techniques described herein.

The slide was then post-exposure baked at 95° C. and developed in SU8 developer, which contains organic solvents. Finally, each slide was characterized on a profilometer (Alpha-Step 500) to measure the height of the fabricated features. Tissue slice thickness was measured up to 5 um tissue, while the photoresist layer was ~7 μm high. FIG. 12 shows the "windows" defined in the photoresist. The dimension defined on the tissue was ~12 μm width, which is smaller than a typical mammalian cell (20 μm).

The tissue section is essentially unchanged after photolithography (see FIG. 12A), except for the discoloration of unmasked areas due to the leeching of the hematoxylin and eosin staining by the organic solvent of the photoresist developer. Some of this discoloration extends under the mask (see FIG. 12A, 12D), likely because the organic solvent is a very small molecule that can penetrate through the tissue to reach the masked areas. An alternative explanation is that the dye can diffuse out into the wells during the digestion and extraction process, leaving the areas of immediate proximity to the wells. It is noted however that the nuclei remain in the unwanted areas but are extracted from the wanted areas—therefore, the unwanted DNA cannot diffuse out the way the dye can.

The laminated areas of the tissue appear far brighter than the exposed tissue (see FIG. 12A) because the refractive index of the photoresist matches the refractive index of the tissue better than air, while the photoresist also mechanically smoothens the surface roughness of the tissue. Thus surface light scattering and refractive divergence are significantly reduced, and the intensity of the detected light is increased over the laminated areas, in comparison to non-laminated tissue.

To extract the exposed tissue, a drop of extractions solution (10 mM Tris-HCl, 2 mM EDTA, pH 8.0, with 10 mg/ml Proteinase K) is placed on top of the masked slide and incubated at 56° C. in a humidity chamber. The Proteinase K digests the tissue, releasing the DNA into solution, which is then suitable for amplification by PCR. The slide after digestion (FIGS. 12B, 12C, 12D) shows the removal, with sharp boundaries defined by the mask, because Proteinase K is a large protein and thus unable to diffuse through the tissue. As seen in FIG. 12B, the digestion is less efficient with smaller features, because the photoresist is hydrophobic and so surface tension works as counter pressure against the entry of the extraction solution into the smaller holes.

The follow sections will describe additional embodiments of methods and devices.

Figure 13:
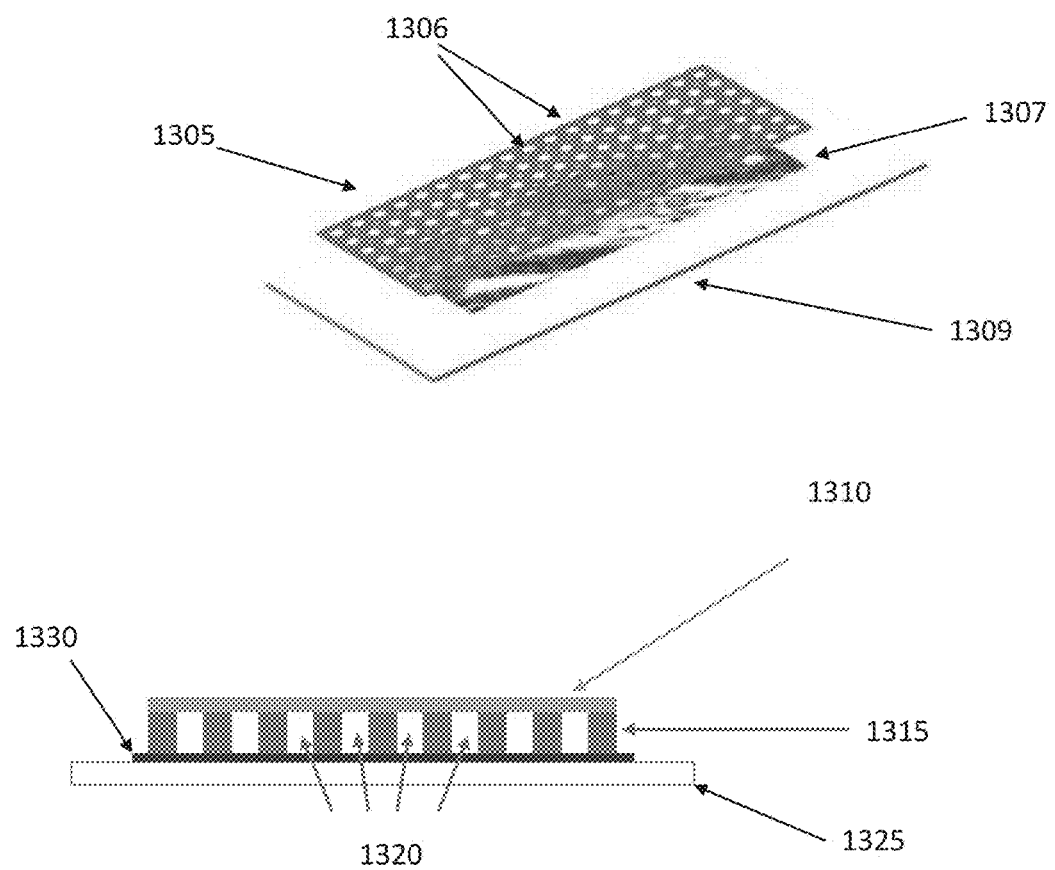
FIG. 13 illustrates an exemplary overlay.

In some embodiments, as visible in FIG. 13, an overlay (1305) may comprise a plurality of openings (1306) that allow access to a tissue sample on a support. In some embodiments, the overlay may comprise a plurality of wells (106) that allow access to the tissue and can also allow filling of the wells with reagents. For example, the overlay (1305) may have a specific thickness to allow the wells (1306) to contain a PCR reagent. When the overlay (1305) is contacted to a tissue (1307), the reagents in the wells are in contact with the tissue (1307), either automatically or by an action performed by a user or machine, such as a pumping action that applies pressure to the reagents in the wells to enable contact with the tissue.

The tissue (1306) may be on a support (1309), such as, for example, a glass support such as a glass slide. A side view of the structure is also visible in FIG. 13, where the overlay (1315) comprises a plurality of access wells (1320). The tissue layer (1330) is between the overlay (1315) and the support (1325). A sealing layer, or seal, (1310) may be positioned on the overlay (1315), for example to prevent the PCR reagents from being contaminated from above.

In some embodiments, an overlay can comprise thousands of openings (for example, 5×5 µm to 1000×1000 µm) which are pre-loaded with reagents enabling multiplex PCR reactions for next generation sequencing (NGS) library generation and subsequent sequencing (and other types of biological reactions). The overlay may have openings with uniform size, or may have different sizes in different areas of the overlay. The overlay can be placed over a tissue slide. An example of tissue slides are the formalin-fixed, paraffin-embedded (FFPE) tissue slides. The FFPE slides can be hematoxylin and eosin stain (H&E) stained. The overlay can be affixed to the tissue creating thousands of individual "reaction wells", and a seal can be placed on top of the overlay to contain the wells and the biological reactions (PCR and other types of reactions). Reactions occur on/with single cells or small clusters of cells depending upon the size of the overlay's openings. Therefore, the size of the openings can be chosen according to the desired application.

In some embodiments, each reaction well is pre-loaded with the same PCR/NGS reagents and a "well-ID" barcode sequence tag. The barcode tag identifies the specific well and enables a unique measurement of each well. Each measurement can be identified by its attached barcode, enabling several applications. For example, the same gene with different mutations can be identified in different regions of the tissue slide. Alternatively, different genes may be identified in different regions, or a combination of different genes and mutations can be identified. The spatial locations of the genes, identified by each unique well barcode, enable a two-dimensional mapping of the tissue slide.

A different pair of barcodes is located at each well and is used to identify the location of the reaction for subsequent analysis. Columns and rows are filled with different barcodes or "well-IDs". For example, referring to FIG. 14, a first barcode A can be filled in all the wells of a first horizontal row (1405), with a second barcode B in a second row (1410) and subsequent barcodes C, D . . . in subsequent rows. For example, the rows can be referred to as an x axis. The columns, or y axis, are also filled with unique barcodes, different from the barcodes of the x axis. For example, in a first column (1415) a barcode 1 can be introduced into all the wells of the first column (1415), with a second barcode 2 in a second column (1420), and subsequent barcodes in subsequent column. The barcodes and columns can be also termed as horizontal (rows) and vertical (columns), even though both rows and columns are in the plane x,y, the plane of the tissue slide. The rows and columns can also be termed as lines, with rows being perpendicular lines, relative to the column lines.

In some embodiments, the assay procedure comprises multiple steps as follows. In a first step, the H&E stained tissue slide is imaged. In some embodiments, the whole slide is imaged through whole slide imaging (WSI).

In a second step, the pre-loaded overlay is placed on-top of the FFPE hematoxylin and eosin stain tissue slide and a seal are placed on top of the overlay. The overlay contains reagents for the desired biological reaction—for example, PCR reaction reagents for NGS library generation, which is then sequenced.

In some embodiments, the assay procedure comprises multiple steps as follows.

In a first step, the H&E stained tissue slide is imaged. In some embodiments, the whole slide is imaged through whole slide imaging (WSI). In a second step, the pre-loaded overlay is placed on-top of the FFPE hematoxylin and eosin stain tissue slide and a seal are placed on top of the overlay. The overlay contains reagents for the desired biological reaction—for example, PCR reaction reagents for NGS library generation, which is then sequenced.

Subsequently, the slide/overlay/seal combination is placed in a thermal cycler to carry-out the desired biological reactions in the individual wells made by placing the overlay on the tissue slide (and seal on the overlay). A thermal cycler, and understood by the person of ordinary skill in the art, is a device that cycles the temperature, for example as required by PCR protocols.

Upon completion of the thermal cycling, the slide/overlay/seal combination can be imaged again. In different embodiments, imaging can be carried out at the same time of the thermal cycling, or at different times, for example at the beginning, and after each cycle, or only at the end of the entirety of cycles. Imaging can be used to check whether the PCR protocol was successful, and whether each thermal cycle is increasing the amount of DNA. Accordingly, the imaging can be used as a tool to verify the positive outcome or positive development of the reactions.

The slide/overlay/seal combination is removed from the thermal cycler and placed into a centrifuge and centrifuged in order to collect the library generated in the biological reaction. The NGS library can then be prepared for sequencing. In some embodiments, optional PCR, clean-up, and sequencer specific preparation may take place at this time as well.

Subsequently, morphogenomic analysis can be carried out—image data is combined with sequencing data and analyzed by a software that maps the sequenced data to the tumor section and cell types.

Figure 14:
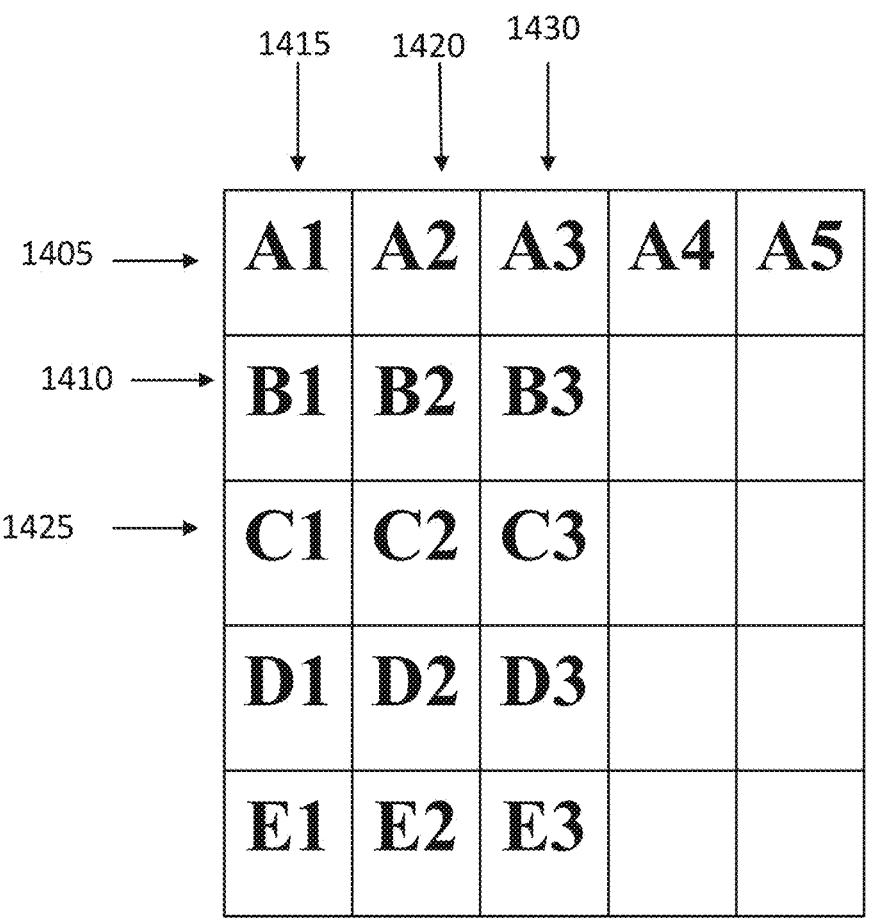
FIG. 14 illustrates an exemplary overlay with barcode mapping.

As visible in FIG. 14, a different pair of barcodes is loaded in each well. To realize this combination, columns and rows are filled with different barcodes. A microfluidic device can accept the different barcoded reagents and distribute them to column or rows. In some embodiments, the device can fill both columns and rows, while in other embodiments, one device is used to fill the columns and one device to fill the rows. For example, in the embodiment wherein the number of columns is equal to the number of rows, the same device can be used for the columns and rows, simply by rotating it by ninety degrees.

Figure 15:
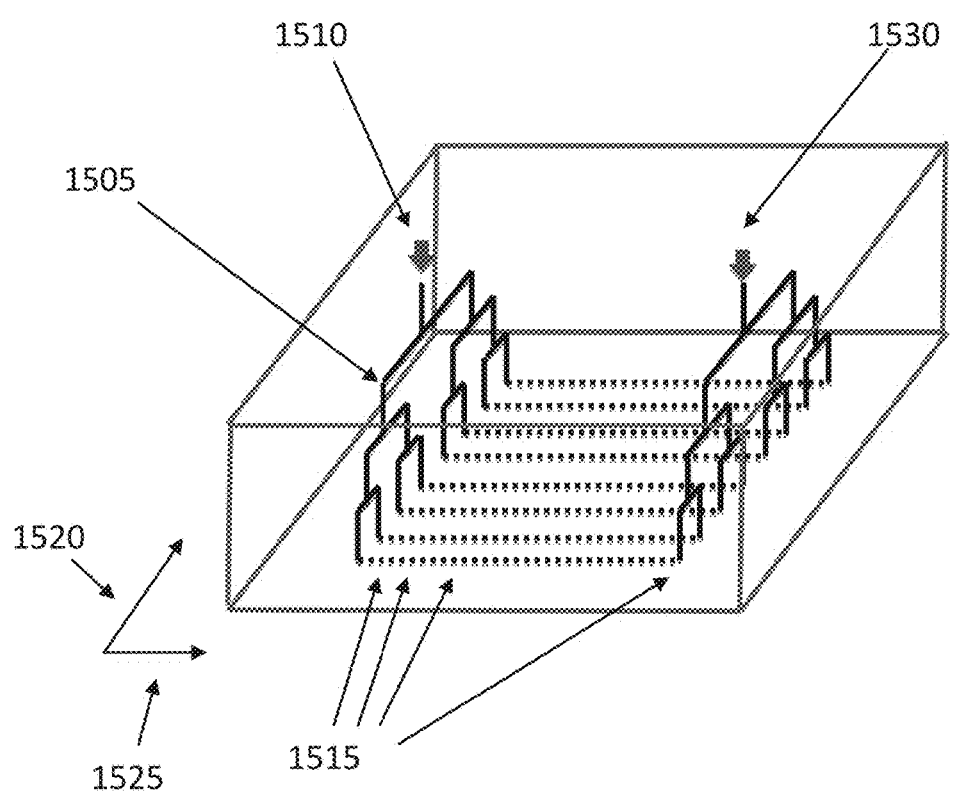
FIG. 15 illustrates an exemplary device to deliver barcodes.

FIG. 15 illustrates an embodiment of a distributor chip that can be used to fill the wells of an overlay. For example, one input (1510) can branch out in multiple channels (1505), for example with a binary tree split. The microfluidic channels branch out until there is one channel for each of the overlay wells in a single row (or column). For example, direction (1520) can be termed the y direction, and direction (1525) can be termed the x direction. Input (1510) is able to fill each overlay well at x=0, along the y axis. Additional microfluidics channels and inputs can be placed at each successive x position (1515), along the x axis. Each of these additional microfluidic channels can fill all the overlay wells along the y axis, at each subsequent x position. These additional structures are not shown in FIG. 15 to avoid cluttering the view, but can be understood by the person of ordinary skill in the art. One input (1530) and binary tree structure at the last x position is illustrated in FIG. 15, as an example. Similarly, the tree channel structures can be rotated by ninety degrees, or the chip itself can be rotated by ninety degrees around a vertical axis, to allow each input to distribute identical reagents to all wells in the same corresponding row along the x axis along a corresponding y position.

The person of ordinary skill in the art will understand that similar, but modified, microfluidic structures may be used, having modified branching or inputs depending on the application. It may also be possible, in some embodiments, to have duplicate barcodes at different inputs, instead of a unique barcode at each input.

The device of FIG. 15, or a similar device, can then be rotated ninety degrees to apply other barcodes, so that the end result is a unique combination of barcodes at each overlay well. For example, in a simple example with four overlay wells, four unique barcodes A, B, 1, 2, are needed, so that the end result would map the four wells with A1, B1, A2, B2. For an example with 25 overlay wells, a total of 10 unique barcodes is needed to have a unique two-dimensional mapping of the 25 wells. In some embodiments, the number of rows and columns is different. In general, a×b overlay wells can be uniquely mapped with a+b unique barcodes. Therefore, the embodiment with each unique barcode and each input allows a completely unique mapping code at each well in the overlay, thus creating a two-dimensional barcode map.

Figure 16:
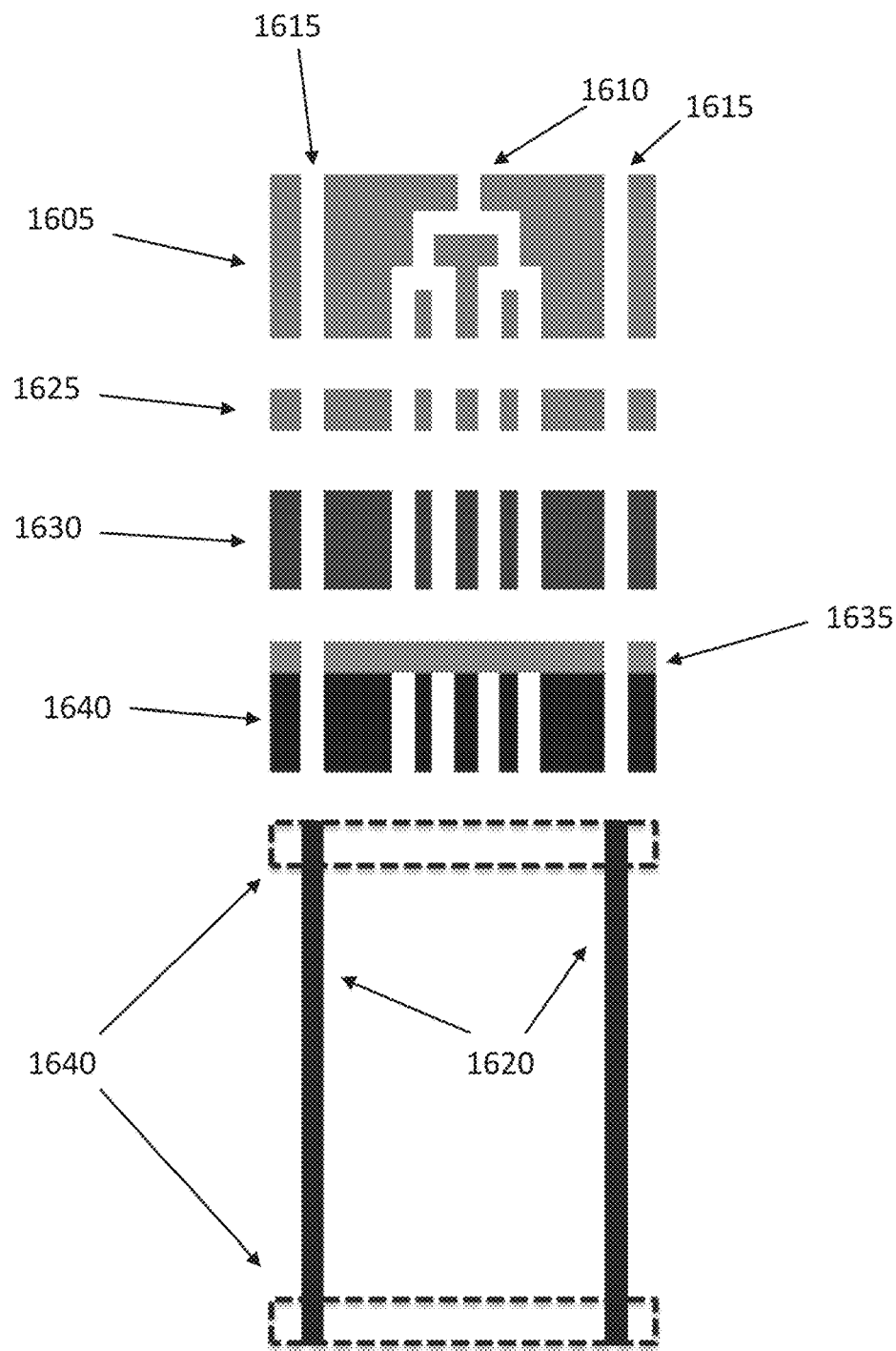
FIG. 16 illustrates an exemplary method on how to prepare an overlay.

FIG. 16 illustrates an exemplary method on how to prepare an overlay. A distributor chip as described in FIG. 15 is illustrated in more details in FIG. 16. Several layers are identified, serving different purposes. In the example of FIG. 16, the binary tree splits only to a total of four overlay wells, for clarity of exposition. A first layer, a top layer, is illustrated (1605). Layer (1605) comprises a binary microfluidic tree (1610), and holes for alignment rods (1615). The holes for the alignment rods continue throughout subsequent layers and allow the insertion of alignment rods (1620). These rods allow the alignment of all layers, so that the layers can be assembled in the correct position, therefore avoiding wobbling and misalignment of the layers. In some embodiments, the rods can be screwed onto the layers and a support at the bottom, to allow compression of the layers during filling of the channels with the reagents. Layer (1610) can be made of different materials, for example polydimethylsiloxane (PDMS) or 3D printed photocurable resins. The channels within the layer can be fabricated by photolithography, etching, 3D printing, or other fabrication techniques.

A next layer (1625), which can be termed the overlay layer, can be made, for example, of silicone. In some embodiments, layer (1625) can be made of silicone-based pressure sensitive adhesive, or silicone coated with adhesive on one or both sides, to allow attachment to other layers or supports. The overlay layer (1625) can comprise, for example, five sub-layers: a plastic foil, e.g. pvc, on top of an adhesive deposited on the top surface of a microfluidic matrix (e.g. made of silicone), followed by another adhesive deposited on the bottom surface of the microfluidic matrix, and finally another foil at the very bottom. The wells of the matrix are defined in all sublayers of the overlay, e.g. by laser cutting them all the way through the overlay. At a later stage, the plastic foils can be removed to allow attachment of the overlay to other layers, supports, tissue, or seals. The next layer (1630) can be termed the receiver chip. The receiver chip (1630) comprises microfluidics channels that match those of the overlay (1625). The channels in chip (1630) can be fabricated, for example, by 3D printing of photocurable resin. The stopper (1635) can be made, for example, of PDMS. An additional layer (1640) has matching microfluidic channel when attached to the stopper, the channels corresponding to the receiver chip. The layer (1640) can be fabricated by 3D printing, e.g. as a copy of the receiver chip.

Figure 17:
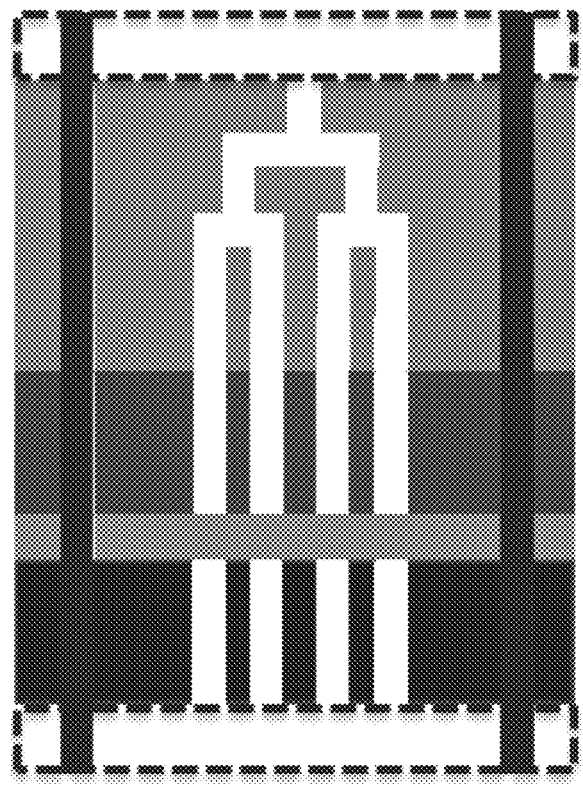
FIG. 17 illustrates an assembled overlay preparation stack.

The layers of FIG. 16 are assembled together. FIG. 17 illustrates the assembled layers from FIG. 16. In FIG. 17, each layer can be readily identified as the corresponding layer of FIG. 16, assembled in the same order. During filling of the microfluidic channels in FIG. 17, the reagents are introduced at the top (1610), and continue to fill the channels below. The liquid reagents are stopped at the stopper, which is permeable to air and water vapor but impermeable to liquid water. Therefore, the air previously present in the channels is displaced by the liquid and exits through the bottom of the device, which is exposed to air to allow evacuation of the gas. With this method, the overlay is filled with reagents without presence of air. Two supporting layers (1640) allow compression of the other layers through the alignment rods. These layers allow passage of air in the bottom channels, and of reagents in the top input, for example through openings.

Figure 18:
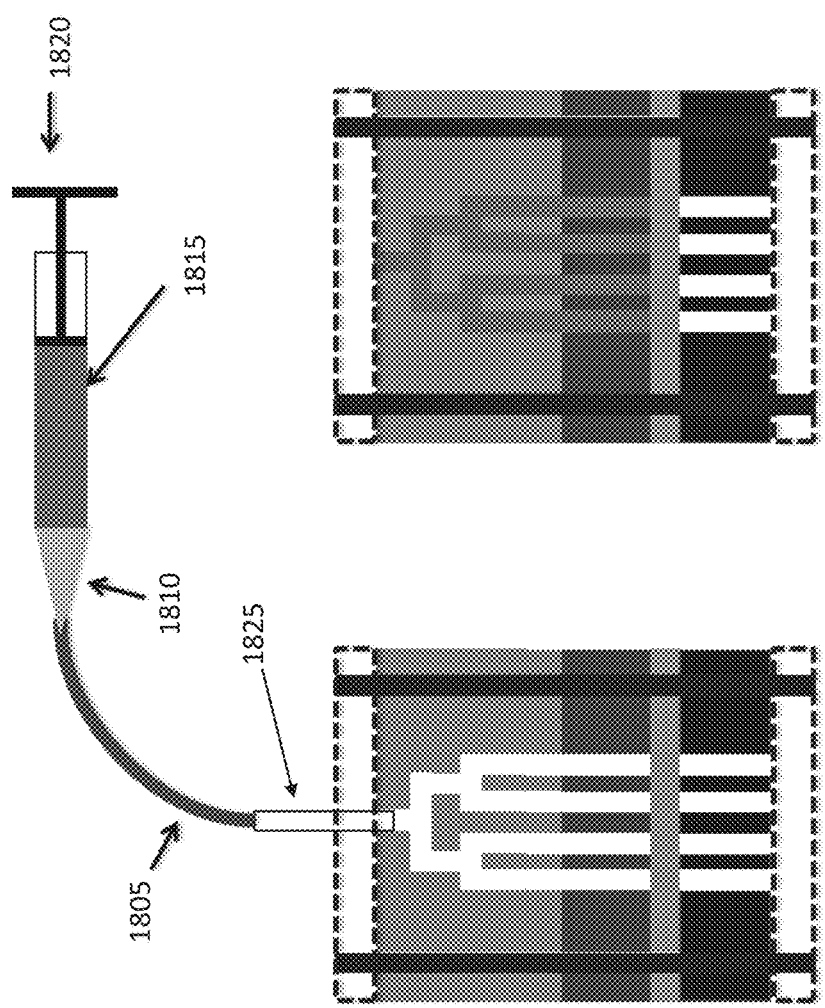
FIG. 18 illustrates filling of an overlay.

FIG. 18 illustrates how the structure of FIG. 17 is filled with reagents. For example, a steel tube (1825) can be inserted in the input channel and connected to a pipe, such as a tygon line (1805), a lure-tub adapted (1810), and a syringe (1820) filled with barcodes and reagents (1815) such as PCR reagents for NGS library generation.

Figure 19:
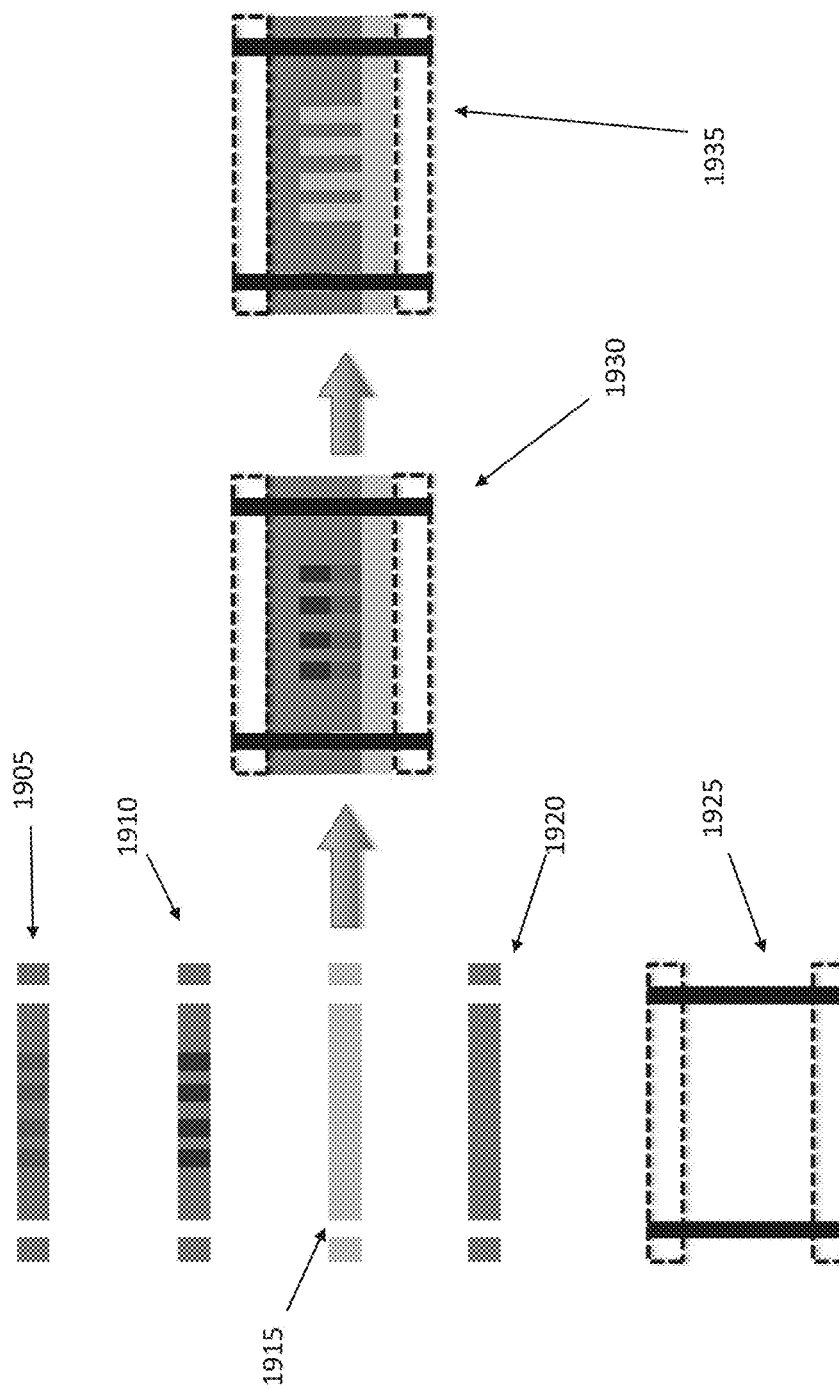
FIG. 19 illustrates assembly of an x and y overlay.

Subsequently, the overlay layers can be separated from the remaining layers, as visible in FIG. 19, (1905, 1910). The liquids inside each overlay layer are held inside the wells by surface tension. Two overlay layers (1905, 1910), each fabricated as described above, can be joined together in order to obtain a unique two-dimensional mapping. One overlay layer contains the x axis barcodes, and the other overlay layer contains the y axis barcodes. The two overlays, therefore, when aligned and assembled, form a unique combination of two barcodes (plus the reagents) in each well of the complete overlay, the complete overlay comprising two overlay layers.

The completed overlay (1905 plus 1910) is attached to the tissue on a tissue slide (1915), and then sealed on the top by a sealing slide (1920), which prevents any liquid leaking from one well to another. The guide rods and frame (1925) can be joined with the other layers to form an overlay-tissue assembly (1930). Upon assembly, the xy barcodes and reagents inside each of the two overlay layers will diffuse and mix (1935), e.g. forming the complete respective library generation reagent mixture in each well.

Figure 20:
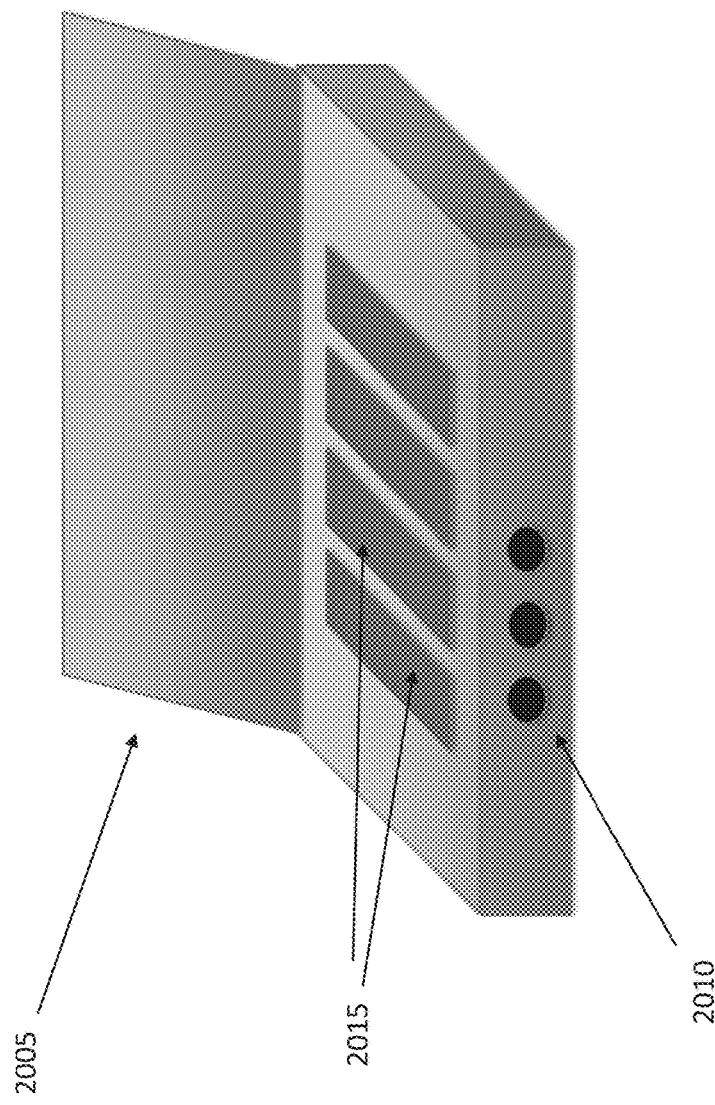
FIG. 20 illustrates an exemplary analysis device.

FIG. 20 illustrates an exemplary device for analyzing tissues slides with an attached overlay. For example, the device may have a lid (2005) that closes over the tissue slides, controls (2010), and housings for a plurality of tissue slides (2015). In some embodiments, the FFPE slides to be analyzed are H&E stained, according to standard protocols. The FFPE slides are placed in the device for imaging. The lid may contain imaging devices, such as light sources and detectors. The bottom may contain a temperature control device, such as a heater and cooler, for example a Peltier heater and cooler.

The device of FIG. 20 is a thermal cycler and fluorescence imager scanner that can detect and analyze each well in the overlay that is placed over a tissue slide. Sequencing can be carried out before or after scanning. The person of ordinary skill in the art will understand that thermal cycling and imaging are carried out as a PCR method is applied. For example, scanning can detect whether the PCR reactions have taken place by receiving a signal from each well. In other embodiments, fluorescence scanning can take place after each thermal cycle. Slides are thermally cycled to create an NGS library used in or for sequencing.

The NGS library can be collected by 'holding' the tissue slide with the overlay and gently centrifugating it into a purpose-build collection area. Since the gene amplicons from each well in the overlay are marked with a unique barcode, the amplicons from all wells can be collected in a single container. The information collected by measuring all the cellular material in the collected solution can be separated and attributed to each well, to form a two-dimensional map, due to the barcode markers.

Figure 21:
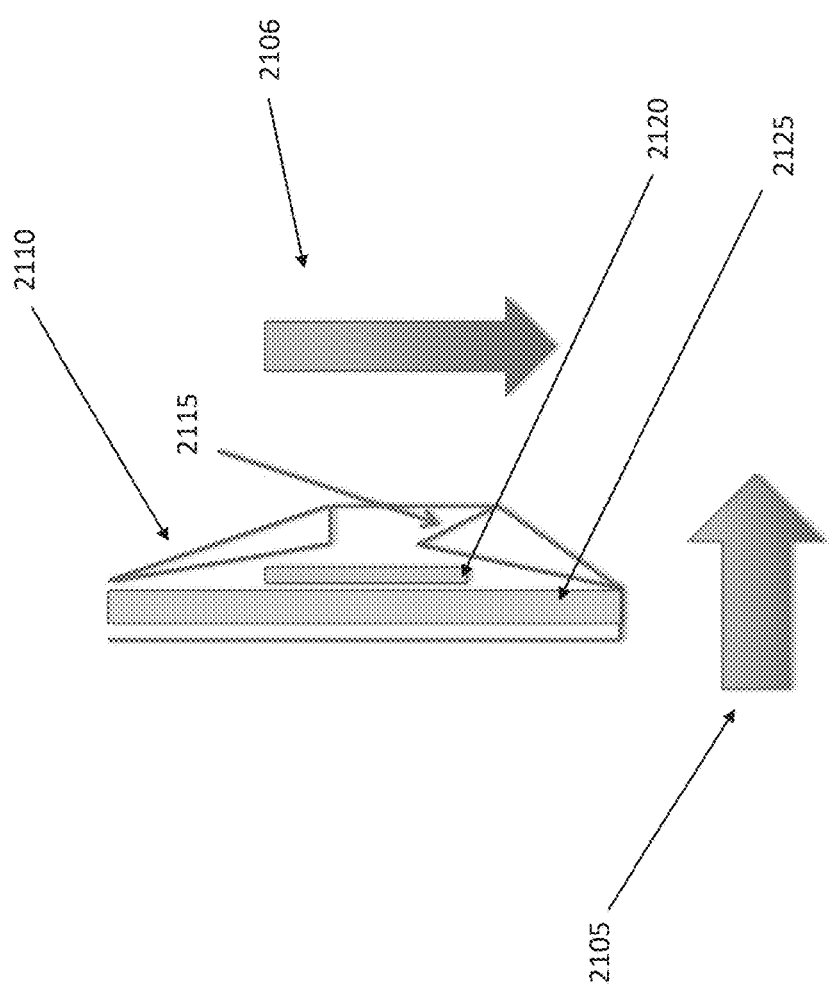
FIG. 21 illustrates an exemplary centrifugation and collection device.

FIG. 21 illustrates an exemplary slide holder (2110) designed to provide support to the slide (2125) and the overlay (2120) while they are centrifuged. The slide holder keeps the overlay in place, and provides an area (2115) for the liquid to collect. FIG. 21 is a side view cross-section of the slide holder (2110) that is spun in a centrifuge. The direction of the centrifugal force is shown by the arrow (2105). The direction of the gravitational force is shown by the arrow (2106). When the slide (2125) is placed in the holder (2110), and spun in a centrifugem the liquid in the overlay (after removal or disruption of the cover on the overlay) will collect in the collection area (2115). As the centrifuge slows down gravity will dominate and the liquid will collect in the area (2115). It can then be easily collected by a pipette or similar device.

In other embodiments, centrifugation is not carried out, and other techniques are used to collect the DNA. For example, after optionally peeling off the overlay, chemical digestion or a combination of digestion and centrifugation could be used to collect all the DNA with the attached barcodes. After collection of the DNA, a purification step can be carried out. The collected DNA can also be referred to as an amplicon, that is a piece of DNA or RNA that is the source or product of the amplification or replication event.

Figure 22:
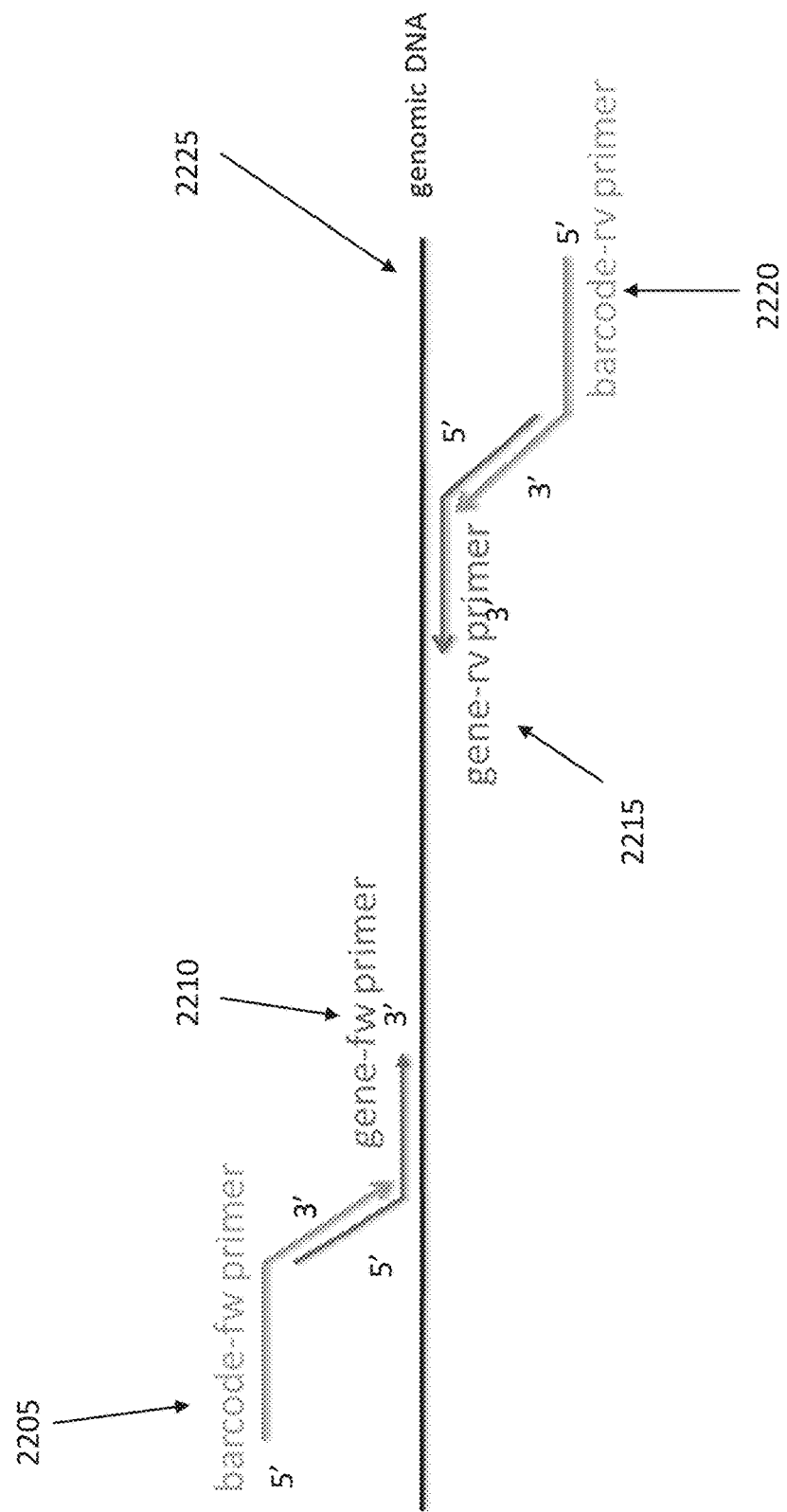
FIG. 22 illustrates an exemplary barcode preparation.

FIG. 22 illustrates an approach on how to prepare barcodes. A barcode forward primer (2205) can be attached to a gene forward primer (2210) on one strand of the genomic DNA (2225), while a barcode reverse primer (2215) can be attached to a gene reverse primer (2220) on one strand of the genomic DNA (2225). The gene primers can combine into panels, while the barcode primers can be generic for any panel.

In the initial round of PCR, only gene primers (2210) (gene forward primer) and (2215) (gene reverse primer) are actively amplifying. These primers have a region at the 3' end designed to be complementary to a specific target gene sequence (gene of interest), and a 5' region that is a 'bridge' sequence. In this embodiment, there are two different bridge sequences for the gene primers: a first bridge sequence at a 5' region of the gene forward primer and a second bridge sequence at a 5' region of the gene reverse primer. In FIG. 22, the 3' end of the gene primers is shown parallel to the genomic DNA target (2225).

In the second round of PCR the products of the first round are amplified, so the reverse complements of the 'bridge sequences' of the gene primers are created. Therefore, after the second round of PCR, the DNA with the reverse complement of the 'bridge' sequences becomes a target for the (2205) and (2220) barcode primers (via the 'bridge' sequences at the 3' ends of the barcode primers). In this embodiment, there are also two different bridge sequences for the barcode primers: a first sequence at the 3' end of the barcode forward primer identical to the first bridge sequence of the gene forward primer and a second bridge sequence at the 3' end of the barcode reverse primer identical to the second bridge sequence of the gene reverse primer. As a result, the gene primers bind to and amplify the target gene sequence through the 3' end that is complementary to the target and the barcode primers amplify the amplification product of the gene primers (i.e. amplicon) through the 3' end bridge sequences of the barcode primers that are complementary to the amplification product of the gene primers.

On their 5' end, barcode primers (2205, 2220) encode the barcode sequence plus additional sequences 5' of that. For instance, in reference to FIG. 14 and FIG. 22, it is possible to consider that the A,B,C . . . barcodes, that is (1405,1410, 1425), are encoded in a series of (2205) barcode primers, and 1,2,3 . . . barcodes, that is (1415,1420,1430), are encoded in a series of (2220) barcode primers.

The term "complementary" as used herein refers to a property of single stranded polynucleotides in which the sequence of the nucleotides on one strand chemically matches the sequence on another strand to form a double stranded polynucleotide. Chemically matching indicates that the nucleobases of the nucleotides in one strand can be non-covalently connected via two or three hydrogen bonds with corresponding nucleobases in another strand.

The person of ordinary skill in the art will understand that some of the sequences above are not described in detail (e.g. the 'bridge' sequences). These sequences are required for and enable the sequencing. For instance, in some embodiments, the 'bridge' sequences correspond to sequencing primer sequences and the 5' most sequence of (2205) and (2220) are sequences required to attach the library to the sequencing device. In principle, it is possible to use one long primer, instead of two shorter primers as described above. However, there are advantages to the method described herein with two short primers. The longer primers (e.g. about 100 base pairs) that could be used as single primers to substitute the two short primers are very expensive to synthesize, several fold more expensive than two shorter primers. Additionally, primers that are very long (100 base pairs) tend not to work very well in PCR. The approach described herein also separates the 'barcode generation' from 'target amplification'. Thus, it makes it easier to design a new library. It is also possible to use a 'common' pool of (2205,2220) primers with unique libraries of (2210,2215) primers, which can simplify the design. In other words, the embodiment of FIG. 22 utilizes two short primers for each side, that is a total of four short primers. In other embodiments, a single long primer could be used for each side, for a total of two long primers. However, the embodiment with short primers has advantages as described above. The primers act as barcodes that enable the two-dimensional positioning of the DNA strand to which the primers are attached to. Since each well of the overlay has a unique combination of two barcodes, the DNA strands in each overlay well can be uniquely identified and assigned to its barcoded spatial position in the overlay.

In other embodiments, it is possible to use Uracil in place of Thymidine in the (2210, 2215) gene primers. Then, if there is a need to do further amplification of the library after it has been collected, it is possible to treat the sample with UDG (uracil DNA glycosylase—which removes uracils, and renders that DNA unamplifiable). Subsequently, it is possible to amplify with primers corresponding to the 5' region (no barcode) of the (2210, 2215) gene primers. This UDG treatment will ensure that no 'new' barcode sequences are added to any amplification products through addition by the (2210,2215) gene primers (which are now effectively destroyed).

Sequencing can be performed on a commercial sequencer. Primer sequences used during amplification can to be customized to the particular sequencer being used. Morphogenomic analysis can be carried out with the devices described in the present disclosure. The placement of the overlay wells over the tissue slides can be automatically determined based on the images of the slide before and after the overlay is placed on it. The genomic data for each well is known based on the barcode pairs from the sequencing. This information is 'combined' to enable, for example, false coloring of the FFPE image based on genomic data. Morphometric parameters determined by software (or manually), can be correlated with and/or visualized by, the software.

For example, integration of genomic and morphological information can reveal tumor heterogeneity. Cancer treatment decisions today are predominantly based upon decades-old histological methods, which more recently have been combined with simple phenotypic or molecular tests. To advance this paradigm, the present disclosure describes a digital molecular morphology platform that integrates histological images with next-generation sequencing (NGS) or PCR data. This method allows the visualization of DNA mutations and RNA expression levels across a histological image, and the correlation of mutational or expression status with cell morphological features. In this way, it is possible to map tumor heterogeneity. The basic approach is to overlay a microstructure on top of H&E-stained FFPE slides to create a large number of tissue-bottomed micro-wells, which can be small as a single cell or contain clusters of cells. Reagents are added to the micro-wells and biochemical reactions are carried out and analyzed in place (PCR) or offline (NGS). In the case of NGS, barcodes are used to reference the resulting sequence back to the tissue image. Software is then used to analyze and visualize the resulting genetic information in the context of the original histological image. In some embodiments, FETE cancer biopsies using targeted cancer genes and gene panels can be used. For example, this approach can be used to measure and visualize KRAS G12V mutational status in colorectal cancer tissues, using both PCR and NGS detection modalities. With the method of the present disclosure, it is possible to efficiently extract DNA from the tissue while maintaining a leak-proof physical integrity from one micro-well to another. Further, it is possible to PCR-amplify DNA in the micro-wells for direct fluorescence detection, or to create libraries for sequencing. Detection of KRAS G12V correlates well with malignant morphological features in the H&E stained tissue, and appears to present a more sensitive way to detect mutations than PCR or NGS from bulk FFPE tissue alone. The methods and devices of the present disclosure can be applied to a variety of research and clinical applications, ranging from assessment of tumor heterogeneity and evolution, to prediction of patient outcome, to post-operative NGS-based characterization of surgical margins. This integration of cellular and molecular data can more fully enable precision medicine to guide the course of treatment and improve individual patient outcomes.

In some embodiments, the microfluidics channel in a distributor chip, with the channel having n end wells, splits n−1 times. Each channel, its input port and its plurality of exit wells runs substantially parallel to either a previous or subsequent channel, depending on the position of the channel in the distributor chip.

The embodiments and examples set forth above are provided to give those of ordinary skill in the art a complete disclosure and description of how to make and use the embodiments of the devices, systems and methods of the disclosure, and are not intended to limit the scope of what the inventors regard as their disclosure.

The examples set forth above are provided to give those of ordinary skill in the art a complete disclosure and description of how to make and use the embodiments of the arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description.

As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

The references in the present application, shown in the reference list below, are incorporated herein by reference in their entirety.

REFERENCES

[1] Shibata D, Hawes D, Li Z H, Hernandez A M, Spruck C H, Nichols P W. Specific genetic analysis of microscopic tissue after selective ultraviolet radiation fractionation and the polymerase chain reaction. Am J Pathol (1992) 141:539-43.

[2] Unger, M. A.; Chou, H. P.; Thorsen, T.; Scherer, A.; Quake, S. R. Monolithic Microfabricated Valves and Pumps by Multilayer Soft Lithography. Science 288, 113-116 (2000).

[3] Kartalov, E P.; Walker, C.; Taylor, C. R.; Scherer, A.; Anderson, W. F. Microfluidic Vias Enable Nested Bioarrays and Autoregulatory Devices in Newtonian Fluids. Proc. Natl. Acad. Sci. USA 103:33, 12280-12284 (2006).

[4] Taylor, Becker, K. F. 'Liquid Morphology': Immunochemical Analysis of Proteins extracted from Formalin Fixed Paraffin Embedded Tissues: combining Proteomics with immunohistochemistry. Applied Immunojhistochem Mol Morph 19, 1-9, 2011.

[5] Shan-Rong Shi, Cheng Liu, Brian M. Balgley, Cheng Lee, and Clive R. Taylor, Protein Extraction from Formalin-fixed, Paraffin-embedded Tissue Sections: Quality Evaluation by Mass Spectrometry. Journal of Histochemistry & Cytochemistry, Volume 54(6): 739-743, 2006.

What is claimed is:

1. A method comprising:
a) providing a distributor chip comprising:
a plurality of microfluidics channels, each microfluidics channel having an input port on a first surface and a plurality of output ports on a second surface opposite the first surface, each microfluidics channel, its input port and its plurality of output ports laying on a plane parallel to a subsequent or previous microfluidics channel, thereby obtaining parallel rows of the output ports on the second surface;
b) providing a first overlay comprising parallel rows of microfluidics wells having positions corresponding to the parallel rows of the output ports;
c) providing a receiver chip comprising parallel rows of microfluidics conduits having positions corresponding to the parallel rows of the microfluidics wells of the first overlay;
d) providing a stopper layer permeable to air and impermeable to water;
e) providing a support layer comprising parallel rows of openings corresponding to the parallel rows of the microfluidics conduits of the receiver chip;
f) positioning the distributor chip on the first overlay, the first overlay on the receiver chip, the receiver chip on the stopper layer, and the stopper layer on the support layer; and
g) aligning the distributor chip, the first overlay, the receiver chip, the stopper layer and the support layer, by aligning the parallel rows of the output ports, the parallel rows of the microfluidics wells, the parallel rows of the microfluidics conduits, and the parallel rows of openings, thereby creating an aligned assembly.

2. The method of claim 1, further comprising: h) inserting a solution in each input port of each microfluidics channel of the plurality of microfluidics channels by pressuring the solution until air exits from the parallel rows of microfluidics conduits of the receiver chip, through the stopper layer, into the parallel rows of openings of the support layer.

3. The method of claim 1, wherein each microfluidics channel binarily splits, between its input port and its plurality of output ports, a number of times equal to the number of its output ports minus one.

4. The method of claim 1, wherein providing a distributor chip is by photolithography or 3D printing, and the distributor chip is made of a photocurable printed resin or polydimethylsiloxane.

5. The method of claim 1, wherein the row overlay is made of silicone, silicon, or glass.

6. The method of claim 1, wherein the row overlay is made of pressure sensitive silicone, and providing the row overlay comprises attaching a pressure sensitive adhesive layer on at least one surface of the row overlay, and attaching at least one plastic foil layer on the at least one pressure sensitive adhesive layer, the at least one plastic foil layer configured to be peeled off to expose the pressure sensitive adhesive layer.

7. The method of claim 1, wherein the stopper layer is made of polydimethylsiloxane.

8. The method of claim 2, wherein the distributor chip, the first overlay, the receiver chip, the stopper layer and the support layer comprise alignment openings, and wherein aligning the distributor chip, the first overlay, the receiver chip, the stopper layer and the support layer comprises inserting alignment rods through the alignment openings.

9. The method of claim 8, wherein each solution inserted in each input port comprises same reagents and a different barcode fir each input port, and further comprising:
  j) removing the first overlay from the aligned assembly, thereby obtaining parallel rows of microfluidics wells, each row having the same reagents and a unique barcode in each row of the parallel rows of microfluidics wells of the first overlay;
  k) providing a second overlay according to steps a)-j), wherein the solution for the second overlay comprises the same reagents but different barcodes than the solution for the first overlay; and
  l) positioning the second overlay on the first overlay, thereby obtaining an assembled overlay, comprising the first overlay and the second overlay, the assembled overlay comprising a plurality of assembled microfluidics wells, each assembled microfluidics well having the same reagents and a unique combination of two barcodes.

10. The method of claim 1, wherein the microfluidics wells have a lateral dimension capable of holding liquids within by surface tension.

11. The method of claim 9, herein the reagents are for polymerase charm reaction.

12. The method of claim 9, further comprising:
attaching the assembled overlay on a tissue slide; and
thermally cycling the tissue slide.

13. The method of claim 12, further comprising imaging the tissue slide.

14. The method of claim 13, wherein the imaging is after each thermal cycle.

15. The method of claim 12, further comprising removing the solution from the assembled overlay.

16. The method of claim 15, wherein the removing is by centrifugating.

17. The method of claim 16, further comprising carrying out morphogenomic analysis for presence of gene mutations by sequencing of gene amplicons including sequences of the unique combinations of two barcodes.

18. The method of claim 12, wherein the tissue slide is a formalin-fixed, paraffin-embedded tissue slide stained with hematoxylin and eosin.

19. The method of claim 18, wherein the assembled overlay comprises at least two thousands wells, each well having lateral dimensions between 5×5 µm and 1000×1000 µm.

20. The method of claim 17, wherein carrying out morphogenomic analysis comprises determining a gene frequency or a mutation frequency in different regions of the tissue slide corresponding to different assembled microfluidics wells.

21. The method of claim 16, further comprising creating a two-dimensional map of genetic information of the tissue slide by assigning the genetic information to each unique combination of two barcodes.

* * * * *